US009238066B2

(12) United States Patent
Gennaro

(10) Patent No.: US 9,238,066 B2
(45) Date of Patent: Jan. 19, 2016

(54) PROTEINS EXPRESSED BY MYCOBACTERIUM TUBERCULOSIS AND NOT BY BCG AND THEIR USE AS DIAGNOSTIC REAGENTS AND VACCINES

(71) Applicant: Rutgers, The State University of New Jersey, New Brunswick, NJ (US)

(72) Inventor: Maria L. Gennaro, New York, NY (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 14/201,308

(22) Filed: Mar. 7, 2014

(65) Prior Publication Data

US 2014/0220600 A1    Aug. 7, 2014

Related U.S. Application Data

(60) Division of application No. 13/893,659, filed on May 14, 2013, now Pat. No. 8,974,800, which is a division of application No. 13/198,108, filed on Aug. 4, 2011, now Pat. No. 8,992,942, which is a continuation of application No. 12/503,717, filed on Jul. 15, 2009, now Pat. No. 8,021,832, which is a continuation of application No. 11/677,502, filed on Feb. 21, 2007, now Pat. No. 7,579,141, which is a division of application No. 10/009,383, filed as application No. PCT/US00/12257 on May 4, 2000, now Pat. No. 7,932,373.

(60) Provisional application No. 60/132,505, filed on May 4, 1999.

(51) Int. Cl.
| | |
|---|---|
| *A61K 39/04* | (2006.01) |
| *A61K 39/02* | (2006.01) |
| *G01N 33/53* | (2006.01) |
| *C07K 14/35* | (2006.01) |
| *G01N 33/569* | (2006.01) |
| *G01N 33/50* | (2006.01) |
| *A61K 38/00* | (2006.01) |
| *A61K 39/00* | (2006.01) |

(52) U.S. Cl.
CPC ............. *A61K 39/04* (2013.01); *C07K 14/35* (2013.01); *G01N 33/5091* (2013.01); *G01N 33/5695* (2013.01); *A61K 38/00* (2013.01); *A61K 39/00* (2013.01); *A61K 2039/53* (2013.01); *Y10S 435/863* (2013.01)

(58) Field of Classification Search
CPC ....... A61K 38/00; A61K 39/04; A61K 39/00; G01N 33/5695
USPC .............. 424/184.1, 185.1, 234.1, 248.1; 435/7.1, 7.2, 253.1

See application file for complete search history.

(56) References Cited

U.S. PATENT DOCUMENTS

| 6,291,190 B1 | 9/2001 | Behr et al. |
|---|---|---|
| 6,436,409 B1 | 8/2002 | Gicquel et al. |
| 7,579,141 B2 | 8/2009 | Gennaro |
| 7,709,211 B2 | 5/2010 | Gennaro |
| 7,932,373 B1 | 4/2011 | Gennaro |
| 8,021,832 B2 | 9/2011 | Gennaro |
| 2007/0224122 A1 | 9/2007 | Gennaro |
| 2007/0224123 A1 | 9/2007 | Gennaro |
| 2010/0016415 A1 | 1/2010 | Gennaro |
| 2011/0052637 A1 | 3/2011 | Gennaro |
| 2012/0107247 A1 | 5/2012 | Gennaro |
| 2013/0251739 A1 | 9/2013 | Gennaro |

FOREIGN PATENT DOCUMENTS

| WO | 97/09428 A2 | 3/1997 |
|---|---|---|
| WO | 97/09429 A2 | 3/1997 |
| WO | 98/16645 A2 | 4/1998 |
| WO | 98/16646 A2 | 4/1998 |
| WO | 98/44119 A1 | 10/1998 |
| WO | 99/04005 A1 | 1/1999 |
| WO | 0011214 A1 | 3/2000 |
| WO | 00/66157 A1 | 11/2000 |
| WO | 0179274 A2 | 10/2001 |
| WO | 03/093307 A2 | 11/2003 |

OTHER PUBLICATIONS

French et al., "What is a Conservative Substitution?." J. Mol. Evol. (1983) 19:171-175.
Berthet et al., (1998), "A Mycobacterium tuberculosis operon encoding ESAT-6 and a novel low-molecular-mass culture filtrate protein(CFP-10)", Microbiol., 144:3195-3203.
Cole et al., "Mycobacterium tuberculosis H37Rv complete genome; segment 160/162", Database EBI, Accession No. AL022120 XP002218539, referring to: Cole et al., (1998) "Deciphering the biology of Mycobacterium tuberculosis from the complete genomesequence", Nature, 393:537-544.
Mahairas et al., 1996, "Molecular Analysis of Genetic Differences between Mycobacterium bovis BCG and Virulent M. Bovis", J. Bacteriol., 178(5):1274-1282.
EP Search Report dated Dec. 23, 2002.
EP Search Report dated Apr. 28, 2003.
Harboe et al., "Evidence for occurrence of the ESAT-6 protein in Mycobacterium tuberculsis virulent Mycobacterium bovis and for its absence in Mycobacterium bovis BCG," Infection and Immunity, 64:16-22 (Jan. 1996).
Opposition of GlaxoSmithKline Biologicals SA filed against European Patent No. EP1214008, Nov. 30, 2009.
Opposition of Statens Serum Institut filed against European Patent No. EP1214088, Jan. 10, 2010.
Wagstaff and Zellweger, Mol. Diag. Ther. (2006) 10(1), 57-63.
Fishi et al., Microbiology (1996) 142, 3147-3161.
Tissot et al., CID (2005) 40, 211-217.

(Continued)

*Primary Examiner* — Rodney P Swartz
(74) *Attorney, Agent, or Firm* — Fox Rothschild LLP; Jianming J. Hao; Michael S. Montgomery

(57) ABSTRACT

The present invention is directed to reagents useful for generating immune responses to *Mycobacterium tuberculosis* and for diagnosing infection and disease in a subject that has been exposed to *M. tuberculosis*.

8 Claims, 8 Drawing Sheets

(56) References Cited

OTHER PUBLICATIONS

Figure 3:
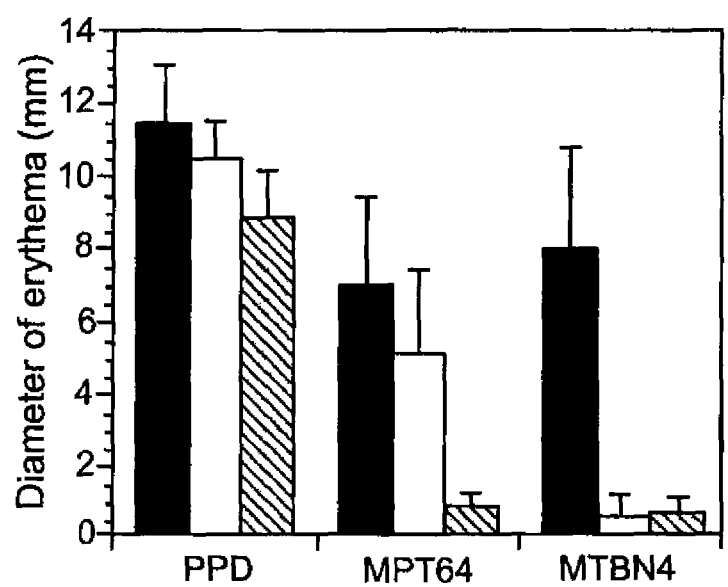

Kinman (1994) current protocols in Immunology 6(19):196; 19-8.
Poulter (1983) clinical & Exprimental Immunology 53:513-520.
Ait-Khaled, Nadia, et al., "Tuberculosis: A Manual for Medical Students", Chapter 1, World Health Organization 2003, p. 1-34.
Letter ot European Patent Office in Reference to Third Party Observations Under Article 115 EPC, Feb. 13, 2009.
Buddle, Bryce M., et al., Differentiation Between Mycobacterium bovis BCG-Vaccinated and M. Bovis-Infected Cattle by Using Recombinant Mycobacterial Antigens, Clin. Diag. Lab. Immunol., vol. 6, No. 1, pp. 1-5, 1999.
Butler, John E., "Enzyme-Linked Immunosorbent Assay", Immunochemistry, 1994, p. 759-803, cited by other.
Cockle, P.J., et al., "Identification of Novel Mycobacterium tuberculosis Antigens with Potentioal as Diagnostic Reagents or Subunit Vaccine Candidiates by Comparative Genomis", Infection and Immunity, vol. 70, No. 12, Dec. 2002, p. 6996-7003.
DiFabio, Simonetta, et al., "Quanitation of Human Influenza Virus-Specific Cytotoxic T Lymphocytes: Correlation of Cytotoxicity and Increased Numbers of IFN-Gamma Producing CD8+ T Cells", International Immunology, vol. 6, No. 1, p. 11-19.
Lalvani, Ajit, et al., "Rapid Effector Fuction in CD8+ Memory T Cells", Journal of Experimental Medicine, vol. 186, No. 6, Sep. 15, 1997, p. 859-865.
Lalvani, Ajit, et al., "Human Cytolytic and Interferon Gamma-Secreting CD8+ T Lymphocytes Specific for Mycobacterium tuberculosis", Proceedings of the National Academy of Sciences of the United States of America, vol. 95, Jan. 1998, p. 270-275.
Lalvani, Ajit, et al., Potent Induction of Focused Th1-Type Cellular and Humoral Immune Responses by RTS, S/SBAS2, a Recombinant Plasmodium faciparum Malaria Vaccine. The Journal of Infection Diseases, vol. 180, 1999, p. 1656-1664.
Lalvani, Ajit, et al., "Rapid Detection of Mycobacterium tuberculosis Infection by Enumeration of Anitgen-specific T Cells", American Journal of Respiratory and Critical Care Medicine, vol. 163, 2001, p. 824-828.
Liu, Xia-Qing, et al., "Evaluation of T-Cell Responses to Novel RD1- and RD2-Encoded Mycobacterium tuberculosis Gene Products for Specific Detection of Human Tuberculosis Infection", Infection and Immunity, May 2004, p. 2574-2581.
Sedgwick, Jonathon, et al., "Detection of Cell-Surface Molecules, Secreted Products of Single Cells and Cellular Proliferation by Enzyme Immunoassay", Journal of Immunological Methods, vol. 150, 1992, p. 159-175.
Andersen et al., "Structure and Mapping onf Antigenic Domains of Protein Antigen b, a 38,000-Molecular-Weight-Protein of Mycobacterium tuberculosis", Infect Immun., vol. 57(8), p. 2481-2488 (Aug. 1989).
Colangeli, R., et al., "MTSA-10, the Product of the RV3874 Gene of Mycobacterium tuberculosis, Elicits Tuberculosis-Specific, Delayed-Type-Hypersensitivity in Guinea Pigs", Infect Immun., vol. 68(2), p. 990-993 (Feb. 2000).
Lyashchenko, K., et al., "Use of Mycobacterium tuberculosis Complex-Specific Antigen Cocktails for a Skin Test for Tuberculosis", Infect Immun., vol. 66(6), p. 3606-3610 (Aug. 1996).
Manca, C., et al., "Molecular Cloning, Purification, and Serological Characterization of MPT63, a Novle Antigen Secreted by Mycobacterium tuberculosis", Infect Immun., vol. 65(1), p. 16-23 (Jan. 1997).
Manca, C., et al., "MTC28, a Novel 28-Kilodalton Proline-Rich Secreted Antigen Specific for the Mycobacterium tuberculosis Complex", Infect Immun., vol. 65(12), p. 4951-4957 (Dec. 1997).
Velaz-Faircloth et al., (1999) Infectino and Immunity 67(8):4243-4250.

Interlocutory Decision in Opposition Proceedings (Art. 101(3)(a) and 106(2) EPC) issued on European Patent Application No. 00928651.5.
Boyum, John E. (1994) Immunochemistry 759-803.
Cole, S.T., et al., "Deciphering the Biology of Mycobacterium tuberculosis from the Complete Genome Sequence."Nature, vol. 396, Nov. 12, 1998.
Abbas, Abul K. et al., Text and Review Series, Cellular and Molecular Immunology. 3rd ed. Philadelphia, PA: W.B. Saunders Co., 1997, Chapter 13, pp. 280-288.
Ravn et al. (Mar. 1999), Journal of Infectious Diseases, vol. 179, pp. 637-645.
Ulrichs et al. (1998), European Journal of Immunology, vol. 28, pp. 3949-3958.
Vordermeier et al. (1991), Journal of Immunology, vol. 147, pp. 1023-1029.
Haslov, K. et al. (1990), Scand. J. Immunol., vol. 31, pp. 503-514.
Shams et al. ( 2004 ), Journal of Immunology, vol. 173, pp. 1966-1977.
Engelhard (1994), Annual Reviews of Immunology, vol. 12, pp. 181-207.
Germain (1995), Annals of the New York Academy of Sciences, vol. 754, pp. 114-125.
Elhay et al. "Delayed-type hypersensitivity responses to ESAT-6 and MPT64 frommycobacterium tuberculosis in the guinea pig." Infection and Immunity (1998): 66(7):3454-3456.
Haga, Shinji et al. (1995) J. of Leucocyte Biology, vol. 57, pp. 221-225.
Roches et al. (1996), Scandinavian Journal of Immunology, vol. 43, pp. 662-670.
Giaxosmith Kline Response filed Aug. 12, 2013 in Opposition of EP1214088.
Declaration of Francois-Xavier Berthet submitted with Glaxo-Smith Kline response filed Aug. 12, 2013 in Opposition of EP1214088.
Declaration of Anja Olsen submitted with GlaxoSmith Kline response filed Aug. 12, 2013 in Opposition of EP1214088.
Response by University of Medicine and Dentistry of New Jersey to Opposition of European Patent No. EP1214088, Sep. 10, 2010.
Lavani et al., "Enumeration of T cells specific for RD1-encoded antigens suggests a high prevalence of latent mycobacterium tuberculosos infection in healthy urban indians." Journal of Infectious Diseases (2001) 183, pp. 469-477.
Pathan et al., High-frequencies of IFN-g—Secreting CD4+ Cells recognizing multiple epitopes in ESAT=6 in tuberculosis patients and healthy contacts, ABSTRACT; submitted with GlaxoSmith Kline response filed Aug. 12, 2013 in Opposition of EP1214088.
E-mail dated May 28, 1998 from jrothei@csl.com.au. submitted with GlaxoSmith Kline response filed Aug. 12, 2013 in Opposition of EP1214088.
Francois-Xavier et al., "Contribution to the study of proteins exported by M. Tuberculosis," EXTRACT.
Olsen et al., Immunological evaluation and protective efficacy of newly identified proteins from M. tuberculosis, Abstract of the 10th International Congress of Immunology, Nov. 1-6, 1998 (New Delhi), 1998 Supplement 1 of The Immunologist.
Information about the result of oral proceedings, European Patent Application No. 00928851.5 (Opposition of European Patent No. EP1214088), Sep. 12, 2012 (downloaded from public espace database on Oct. 2, 2012).
Response to Communication (Office Action) (including claim amendments) in European Patent Application No. 09158386.4 (published EP2087906) dated May 20, 2011 (downloaded from public espacenet database on Oct. 2, 2012).
Communication (Office Action) in European Patent Application No. 09158386.4 (published EP2087906) dated Oct. 1, 2012 (downloaded from public espacenet database on Oct. 2, 2012).

MTBN1
MTAEPEVRTLREVVLDQLGTAESRAYKMWLPPLTNPVPLNELIARDRRQPLRFALGIMDE
PRRHLQDVWGVDVSGAGGNIGIGGAPQTGKSTLLQTMVMSAAATHSPRNVQFYCIDLGGG
GLIYLENLPHVGGVANRSEPDKVNRVVAEMQAVMRQRETTFKEHRVGSIGMYRQLRDDPS
QPVASDPYGDVFLIIDGWPGFVGEFPDLEGQVQDLAAQGLAFGVHVIISTPRWTELKSRV
RDYLGTKIEFRLGDVNETQIDRITREIPANRPGRAVSMEKHHLMIGVPRFDGVHSADNLV
EAITAGVTQIASQHTEQAPPVRVLPERIHLHELDPNPPGPESDYRTRWEIPIGLRETDLT
PAHCHMHTNPHLLIFGAAKSGKTTIAHAIARAICARNSPQQVRFMLADYRSGLLDAVPDT
HLLGAGAINRNSASLDEAVQALAVNLKKRLPPTDLTTAQLRSRSWWSGPDVVLLVDDWHM
IVGAAGGMPPMAPLAPLLPAAADIGLHIIVTCQMSQAYKATMDKFVGAAFGSGAPTMFLS
GEKQEFPSSEFKVKRRPPGQAFLVSPDGKEVIQAPYIEPPEEVFAAPPSAG

MTBN2
MEKMSHDPIAADIGTQVSDNALHGVTAGSTALTSVTGLVPAGADEVSAQAATAFTSEGIQ
LLASNASAQDQLHRAGEAVQDVARTYSQIDDGAAGVFAE

MTBN3
MLWHAMPPELNTARLMAGAGPAPMLAAAAGWQTLSAALDAQAVELTARLNSLGEAWTGGG
SDKALAAATPMVVWLQTASTQAKTRAMQATAQAAAYTQAMATTPSLPEIAANHITQAVLT
ATNFFGINTIPIALTEMDYFIRMWNQAALAMEVYQAETAVNTLFEKLEPMASILDPGASQ
STTNPIFGMPSPGSSTPVGQLPPAATQTLGQLGEMSGPMQQLTQPLQQVTSLFSQVGGTG
GGNPADEEAAQMGLLGTSPLSNHPLAGGSGPSAGAGLLRAESLPGAGGSLTRTPLMSQLI
EKPVAPSVMPAAAAGSSATGGAAPVGAGAMGQGAQSGGSTRPGLVAPAPLAQEREEDDED
DWDEEDDW

MTBN4
MAEMKTDAATLAQEAGNFERISGDLKTQIDQVESTAGSLQGQWRGAAGTAAQAAVVRFQE
AANKQKQELDEISTNIRQAGVQYSRADEEQQQALSSQMGF

MTBN5
MAADYDKLFRPHEGMEAPDDMAAQPFFDPSASFPPAPASANLPKPNGQTPPPTSDDLSER
FVSAPPPPPPPPPPPPPTPMPIAAGEPPSPEPAASKPPTPPMPIAGPEPAPPKPPTPPMP
IAGPEPAPPKPPTPPMPIAGPAPTPTESQLAPPRPPTPQTPTGAPQQPESPAPHVPSHGP
HQPRRTAPAPPWAKMPIGEPPPAPSRPSASPAEPPTRPAPQHSRRARRGHRYRTDTERNV
GKVATGPSIQARLRAEEASGAQLAPGTEPSPAPLGQPRSYLAPPTRPAPTEPPPSPSPQR
NSGRRAERRVHPDLAAQHAAAQPDSITAATTGGRRRKRAAPDLDATQKSLRPAAKGPKVK
KVKPQKPKATKPPKVVSQRGWRHWVHALTRINLGLSPDEKYELDLHARVRRNPRGSYQIA
VVGLKGGAGKTTLTAALGSTLAQVRADRILALDADPGAGNLADRVGRQSGATIADVLAEK
ELSHYNDIRAHTSVNAVNLEVLPAPEYSSAQRALSDADWHFIADPASRFYNLVLADCGAG
FFDPLTRGVLSTVSGVVVVASVSIDGAQQASVALDWLRNNGYQDLASRACVVINHIMPGE
PNVAVKDLVRHFEQQVQPGRVVVMPWDRHIAAGTEISLDLLDPIYKRKVLELAAALSDDF
ERAGRR

FIG 1A

MTBN6
LSAPAVAAGPTAAGATAARPATTRVTILTGRRMTDLVLPAAVPMETYIDDTVAVLSEVLE
DTPADVLGGFDFTAQGVWAFARPGSPPLKLDQSLDDAGVVDGSLLTLVSVSRTERYRPLV
EDVIDAIAVLDESPEFDRTALNRFVGAAIPLLTAPVIGMAMRAWWETGRSLWWPLAIGIL
GIAVLVGSFVANRFYQSGHLAECLLVTTYLLIATAAALAVPLPRGVNSLGAPQVAGAATA
VLFLTLMTRGGPRKRHELASFAVITAIAVIAAAAFGYGYQDWVPAGGIAFGLFIVTNAA
KLTVAVARIALPPIPVPGETVDNEELLDPVATPEATSEETPTWQAIIASVPASAVRLTER
SKLAKQLLIGYVTSGTLILAAGAIAVVVRGHFFVHSLVVAGLITTVCGFRSRLYAERWCA
WALLAATVAIPTGLTAKLIIWYPHYAWLLLSVYLTVALVALVVVGSMAHVRRVSPVVKRT
LELIDGAMIAAIIPMLLWITGVYDTVRNIRF

MTBN7
MAEPLAVDPTGLSAAAAKLAGLVFPQPPAPIAVSGTDSVVAAINETMPSIESLVSDGLPG
VKAALTRTASNMNAAADVYAKTDQSLGTSLSQYAFGSSGEGLAGVASVGGQPSQATQLLS
TPVSQVTTQLGETAAELAPRVVATVPQLVQLAPHAVQMSQNASPIAQTISQTAQQAAQSA
QGGSGPMPAQLASAEKPATEQAEPVHEVTNDDQGDQGDVQPAEVVAAARDEGAGASPGQQ
PGGGVPAQAMDTGAGARPAASPLAAPVDPSTPAPSTTTTL

MTBN8
MSITRPTGSYARQMLDPGGWVEADEDTFYDRAQEYSQVLQRVTDVLDTCRQQKGHVFEGG
LWSGGAANAANGALGANINQLMTLQDYLATVITWHRHIAGLIEQAKSDIGNNVDGAQREI
DILENDPSLDADERHTAINSLVTATHGANVSLVAETAERVLESKNWKPPKNALEDLLQQK
SPPPPDVPTLVVPSPGTPGTPGTPITPGTPITPGTPITPIPGAPVTPITPTPGTPVTPVT
PGKPVTPVTPVKPGTPGEPTPITPVTPPVAPATPATPATPVTPAPAPHPQPAPAPAPSPG
PQPVTPATPGPSGPATPGTPGGEPAPHVKPAALAEQPGVPGQHAGGGTQSGPAHADESAA
SVTPAAASGVPGARAAAAPSGTAVGAGARSSVGTAAASGAGSHAATGRAPVATSDKAAA
PSTRAASARTAPPARPPSTDHIDKPDRSESADDGTPVSMIPVSAARAARDAATAAASARQ
RGRGDALRLARRIAAALNASDNNAGDYGFFWITAVTTDGSIVVANSYGLAYIPDGMELPN
KVYLASADHAIPVDEIARCATYPVLAVQAWAAFHDMTLRAVIGTAEQLASSDPGVAKIVL
EPDDIPESGKMTGRSRLEVVDPSAAAQLADTTDQRLLDLLPPAPVDVNPPGDERHMLWFE
LMKPMTSTATGREAAHLRAFRAYAAHSQEIALHQAHTATDAAVQRVAVADWLYWQYVTGL
LDRALAAAC

FIG 1B mtbn1

```
1     atgactgctg aaccggaagt acggacgctg cgcgaggttg tgctggacca
51    gctcggcact gctgaatcgc gtgcgtacaa gatgtggctg ccgccgttga
101   ccaatccggt cccgctcaac gagctcatcg cccgtgatcg gcgacaaccc
151   ctgcgatttg ccctggggat catggatgaa ccgcgccgcc atctacagga
201   tgtgtggggc gtagacgttt ccggggccgg cggcaacatc ggtattgggg
251   gcgcacctca aaccgggaag tcgacgctac tgcagacgat ggtgatgtcg
301   gccgccgcca cacactcacc gcgcaacgtt cagttctatt gcatcgacct
351   aggtggcggc gggctgatct atctcgaaaa ccttccacac gtcggtgggg
401   tagccaatcg gtccgagccc gacaaggtca accgggtggt cgcagagatg
451   caagccgtca tgcggcaacg ggaaaccacc ttcaaggaac accgagtggg
501   ctcgatcggg atgtaccggc agctgcgtga cgatccaagt caacccgttg
551   cgtccgatcc atacggcgac gtctttctga tcatcgacgg atggcccggt
601   tttgtcggcg agttccccga ccttgagggg caggttcaag atctggccgc
651   ccaggggctg gcgttcggcg tccacgtcat catctccacg ccacgctgga
701   cagagctgaa gtcgcgtgtt cgcgactacc tcggcaccaa gatcgagttc
751   cggcttggtg acgtcaatga acccagatc gaccggatta cccgcgagat
801   cccggcgaat cgtccgggtc gggcagtgtc gatggaaaag caccatctga
851   tgatcggcgt gcccaggttc gacggcgtgc acagcgccga taacctggtg
901   gaggcgatca ccgcggggt gacgcagatc gcttcccagc acaccgaaca
951   ggcacctccg gtgcgggtcc tgccggagcg tatccacctg cacgaactcg
1001  acccgaaccc gccgggacca gagtccgact accgcactcg ctgggagatt
1051  ccgatcggct tgcgcgagac ggacctgacg ccggctcact gccacatgca
1101  cacgaacccg cacctactga tcttcggtgc ggccaaatcg gcaagacga
1151  ccattgccca cgcgatcgcg cgcgccattt gtgcccgaaa cagtccccag
1201  caggtgcggt tcatgctcgc ggactaccgc tcgggcctgc tggacgcggt
1251  gccggacacc catctgctgg cgccggcgc gatcaaccgc aacagcgcgt
1301  cgctagacga ggccgttcaa gcactggcgg tcaacctgaa gaagcggttg
1351  ccgccgaccg acctgacgac ggcgcagcta cgctcgcgtt cgtggtggag
1401  cggatttgac gtcgtgcttc tggtcgacga ttggcacatg atcgtgggtg
1451  ccgccggggg gatgccgccg atggaccgc tggccccgtt attgccggcg
1501  gcggcagata tcgggttgca catcattgtc acctgtcaga tgagccaggc
1551  ttacaaggca accatggaca agttcgtcgg cgccgcattc gggtcgggcg
1601  ctccgacaat gttcctttcg ggcgagaagc aggaattccc atccagtgag
1651  ttcaaggtca agcggcgccc ccctggccag gcatttctcg tctcgccaga
1701  cggcaaagag gtcatccagg cccctacat cgagcctcca gaagaagtgt
1751  tcgcagcacc cccaagcgcc ggttaa
``` mtbn2

```
1     atggaaaaaa tgtcacatga tccgatcgct gccgacattg gcacgcaagt
51    gagcgacaac gctctgcacg gcgtgacggc cggctcgacg gcgctgacgt
101   cggtgaccgg gctggttccc gcggggccg atgaggtctc cgcccaagcg
151   gcgacggcgt tcacatcgga gggcatccaa ttgctggctt ccaatgcatc
201   ggcccaagac cagctccacc gtgcgggcga agcggtccag gacgtcgccc
251   gcacctattc gcaaatcgac gacggcgccg ccggcgtctt cgccgaatag
```

FIG 2A mtbn3
```
1     atgctgtggc acgcaatgcc accggagcta ataccgcac  ggctgatggc
51    cggcgcgggt ccggctccaa tgcttgcggc ggccgcggga tggcagacgc
101   tttcggcggc tctggacgct caggccgtcg agttgaccgc gcgcctgaac
151   tctctgggag aagcctggac tggaggtggc agcgacaagg cgcttgcggc
201   tgcaacgccg atggtggtct ggctacaaac cgcgtcaaca caggccaaga
251   cccgtgcgat gcaggcgacg gcgcaagccg cggcatacac ccaggccatg
301   gccacgacgc cgtcgctgcc ggagatcgcc gccaaccaca tcacccaggc
351   cgtccttacg gccaccaact tcttcggtat caacacgatc ccgatcgcgt
401   tgaccgagat ggattatttc atccgtatgt ggaaccaggc agccctggca
451   atggaggtct accaggccga gaccgcggtt aacacgcttt tcgagaagct
501   cgagccgatg gcgtcgatcc ttgatcccgg cgcgagccag agcacgacga
551   acccgatctt cggaatgccc tccctggca gctcaacacc ggttggccag
601   ttgccgccgg cggctaccca gaccctcggc caactgggtg agatgagcgg
651   cccgatgcag cagctgaccc agccgctgca gcaggtgacg tcgttgttca
701   gccaggtggg cggcaccggc ggcggcaacc cagccgacga ggaagccgcg
751   cagatgggcc tgctcggcac cagtccgctg tcgaaccatc cgctggctgg
801   tggatcaggc cccagcgcgg gcgcgggcct gctgcgcgcg gagtcgctac
851   ctggcgcagg tgggtcgttg acccgcacgc cgctgatgtc tcagctgatc
901   gaaaagccgg ttgccccctc ggtgatgccg gcggctgctg ccggatcgtc
951   ggcgacgggt ggcgccgctc cggtgggtgc gggagcgatg ggccagggtg
1001  cgcaatccgg cggctccacc aggccgggtc tggtcgcgcc ggcaccgctc
1051  gcgcaggagc gtgaagaaga cgacgaggac gactgggacg aagaggacga
1101  ctggtga
``` mtbn4
```
1     atggcagaga tgaagaccga tgccgctacc ctcgcgcagg aggcaggtaa
51    tttcgagcgg atctccggcg acctgaaaac ccagatcgac caggtggagt
101   cgacggcagg ttcgttgcag ggccagtggc gcggcgcggc ggggacggcc
151   gcccaggccg cggtggtgcg cttccaagaa gcagccaata agcagaagca
201   ggaactcgac gagatctcga cgaatattcg tcaggccggc gtccaatact
251   cgagggccga cgaggagcag cagcaggcgc tgtcctcgca aatgggcttc
301   tga
``` mtbn5
```
1     atggcggccg actacgacaa gctcttccgg ccgcacgaag gtatggaagc
51    tccggacgat atggcagcgc agccgttctt cgaccccagt gcttcgtttc
101   cgccggcgcc cgcatcggca aacctaccga agcccaacgg ccagactccg
151   cccccgacgt ccgacgacct gtcggagcgg ttcgtgtcgg cccgccgcc
201   gccaccccca cccccacctc cgcctccgcc aactccgatg ccgatcgccg
251   caggagagcc gccctgccg gaaccggccg catctaaacc acccacaccc
301   cccatgccca tgccggacc cgaaccggcc ccacccaaac cacccacac
351   cccatgccc atcgccggac ccgaaccggc ccacccaaa ccacccacac
401   ctccgatgcc catcgccgga cctgcaccca cccaaccga atcccagttg
```

FIG 2B

```
451   gcgccccca gaccaccgac accacaaacg ccaaccggag cgccgcagca
501   accggaatca ccggcgcccc acgtaccctc gcacgggcca catcaacccc
551   ggcgcaccgc accagcaccg ccctgggcaa agatgccaat cggcgaaccc
601   ccgcccgctc cgtccagacc gtctgcgtcc ccggccgaac caccgacccg
651   gcctgccccc caacactccc gacgtgcgcg ccggggtcac cgctatcgca
701   cagacaccga acgaaacgtc gggaaggtag caactggtcc atccatccag
751   gcgcggctgc gggcagagga agcatccggc gcgcagctcg ccccggaac
801   ggagccctcg ccagcgccgt tgggccaacc gagatcgtat ctggctccgc
851   ccacccgccc cgcgccgaca gaacctcccc ccagcccctc gccgcagcgc
901   aactccggtc ggcgtgccga gcgacgcgtc caccccgatt tagccgccca
951   acatgccgcg gcgcaacctg attcaattac ggccgcaacc actggcggtc
1001  gtcgccgcaa gcgtgcagcg ccggatctcg acgcgacaca gaaatcctta
1051  aggccggcgg ccaaggggcc gaaggtgaag aaggtgaagc cccagaaacc
1101  gaaggccacg aagccgccca aagtggtgtc gcagcgcggc tggcgacatt
1151  gggtgcatgc gttgacgcga atcaacctgg gcctgtcacc cgacgagaag
1201  tacgagctgg acctgcacgc tcgagtccgc cgcaatcccc gcgggtcgta
1251  tcagatcgcc gtcgtcggtc tcaaaggtgg ggctggcaaa accacgctga
1301  cagcagcgtt ggggtcgacg ttggctcagg tgcgggccga ccggatcctg
1351  gctctagacg cggatccagg cgccggaaac ctcgccgatc gggtagggcg
1401  acaatcgggc gcgaccatcg ctgatgtgct tgcagaaaaa gagctgtcgc
1451  actacaacga catccgcgca cacactagcg tcaatgcggt caatctggaa
1501  gtgctgccgg caccggaata cagctcggcg cagcgcgcgc tcagcgacgc
1551  cgactggcat ttcatcgccg atcctgcgtc gaggttttac aacctcgtct
1601  tggctgattg tggggccggc ttcttcgacc cgctgacccg cggcgtgctg
1651  tccacggtgt ccggtgtcgt ggtcgtggca agtgtctcaa tcgacggcgc
1701  acaacaggcg tcggtcgcgt tggactggtt gcgcaacaac ggttaccaag
1751  atttggcgag ccgcgcatgc gtggtcatca atcacatcat gccgggagaa
1801  cccaatgtcg cagttaaaga cctggtgcgg catttcgaac agcaagttca
1851  acccggccgg gtcgtggtca tgccgtggga caggcacatt gcggccggaa
1901  ccgagatttc actcgacttg ctcgacccta tctacaagcg caaggtcctc
1951  gaattggccg cagcgctatc cgacgatttc gagagggctg gacgtcgttg
2001  a
``` mtbn6
```
1     ttgagcgcac ctgctgttgc tgctggtcct accgccgcgg gggcaaccgc
51    tgcgcggcct gccaccaccc gggtgacgat cctgaccggc agacggatga
101   ccgatttggt actgccagcg gcggtgccga tggaaactta tattgacgac
151   accgtcgcgg tgctttccga ggtgttggaa gacaccgcgg ctgatgtact
201   cggcggcttc gactttaccg cgcaaggcgt gtgggcgttc gctcgtcccg
251   gatcgccgcc gctgaagctc gaccagtcac tcgatgacgc cggggtggtc
301   gacgggtcac tgctgactct ggtgtcagtc agtcgcaccg agcgctaccg
351   accgttggtc gaggatgtca tcgacgcgat cgccgtgctt gacgagtcac
401   ctgagttcga ccgcacggca ttgaatcgct tgtggggc ggcgatcccg
451   cttttgaccg cgccgtcat cgggatggcg atgcgggcgt ggtgggaaac
501   tgggcgtagc ttgtggtggc cgttggcgat tggcatcctg gggatcgctg
```

FIG 2C

```
551   tgctggtagg cagcttcgtc gcgaacaggt tctaccagag cggccacctg
601   gccgagtgcc tactggtcac gacgtatctg ctgatcgcaa ccgccgcagc
651   gctggccgtg ccgttccgc gcggggtcaa ctcgttgggg cgccacaag
701   ttgccggcgc cgctacggcc gtgctgtttt tgaccttgat gacgcgggc
751   ggccctcgga agcgtcatga gttggcgtcg tttgccgtga tcaccgctat
801   cgcggtcatc gcggccgccg ctgccttcgg ctatggatac caggactggg
851   tccccgcggg ggggatcgca ttcgggctgt tcattgtgac gaatgcggcc
901   aagctgaccg tcgcggtcgc gcggatcgcg ctgccgccga ttccggtacc
951   cggcgaaacc gtggacaacg aggagttgct cgatcccgtc gcgaccccgg
1001  aggctaccag cgaagaaacc ccgacctggc aggccatcat cgcgtcggtg
1051  cccgcgtccg cggtccggct caccgagcgc agcaaactgg ccaagcaact
1101  tctgatcgga tacgtcacgt cgggcaccct gattctggct gccggtgcca
1151  tcgcggtcgt ggtgcgcggg cacttctttg tacacagcct ggtggtcgcg
1201  ggtttgatca cgaccgtctg cggatttcgc tcgcggcttt acgccgagcg
1251  ctggtgtgcg tgggcgttgc tggcggcgac ggtcgcgatt ccgacgggtc
1301  tgacggccaa actcatcatc tggtacccgc actatgcctg gctgttgttg
1351  agcgtctacc tcacggtagc cctggttgcg ctcgtggtgg tcgggtcgat
1401  ggctcacgtc cggcgcgttt caccggtcgt aaaacgaact ctggaattga
1451  tcgacggcgc catgatcgct gccatcattc ccatgctgct gtggatcacc
1501  ggggtgtacg acacggtccg caatatccgg ttctga mtbn7
1     atggctgaac cgttggccgt cgatcccacc ggcttgagcg cagcggccgc
51    gaaattggcc ggcctcgttt ttccgcagcc tccggcgccg atcgcggtca
101   gcggaacgga ttcggtggta gcagcaatca acgagaccat gccaagcatc
151   gaatcgctgg tcagtgacgg gctgcccggc gtgaaagccg ccctgactcg
201   aacagcatcc aacatgaacg cggcggcgga cgtctatgcg aagaccgatc
251   agtcactggg aaccagtttg agccagtatg cattcggctc gtcgggcgaa
301   ggcctggctg gcgtcgcctc ggtcggtggt cagccaagtc aggctaccca
351   gctgctgagc acccgtgt cacaggtcac gacccagctc ggcgagacgg
401   ccgctgagct ggcaccccgt gttgttgcga cggtgccgca actcgttcag
451   ctggctccgc acgccgttca gatgtcgcaa aacgcatccc ccatcgctca
501   gacgatcagt caaaccgccc aacaggccgc ccagagcgcg cagggcggca
551   gcggcccaat gcccgcacag cttgccagcg ctgaaaaacc ggccaccgag
601   caagcggagc cggtccacga agtgacaaac gacgatcagg gcgaccaggg
651   cgacgtgcag ccggccgagg tcgttgccgc ggcacgtgac gaaggcgccg
701   gcgcatcacc gggccagcag cccggcgggg gcgttcccgc gcaagccatg
751   gataccggag ccggtgcccg cccagcggcg agtccgctgg cggccccgt
801   cgatccgtcg actccggcac cctcaacaac cacaacgttg tag
```

FIG 2D mtbn8

```
1     atgagtatta ccaggccgac gggcagctat gccagacaga tgctggatcc
51    gggcggctgg gtggaagccg atgaagacac tttctatgac cgggcccagg
101   aatatagcca ggttttgcaa agggtcaccg atgtattgga cacctgccgc
151   cagcagaaag gccacgtctt cgaaggcggc ctatggtccg gcggcgccgc
201   caatgctgcc aacggcgccc tgggtgcaaa catcaatcaa ttgatgacgc
251   tgcaggatta tctcgccacg gtgattacct ggcacaggca tattgccggg
301   ttgattgagc aagctaaatc cgatatcggc aataatgtgg atggcgctca
351   acgggagatc gatatcctgg agaatgaccc tagcctggat gctgatgagc
401   gccataccgc catcaattca ttggtcacgg cgacgcatgg ggccaatgtc
451   agtctggtcg ccgagaccgc tgagcgggtg ctggaatcca agaattggaa
501   acctccgaag aacgcactcg aggatttgct tcagcagaag tgccgccac
551   ccccagacgt gcctaccctg gtcgtgccat ccccgggcac accgggcaca
601   ccgggaaccc cgatcacccc gggaacccg atcaccccgg aaccccaat
651   cacacccatc ccgggagcgc cggtaactcc gatcacacca acgcccggca
701   ctcccgtcac gccggtgacc ccgggcaagc cggtcacccc ggtgaccccg
751   gtcaaaccgg gcacaccagg cgagccaacc ccgatcacgc cggtcacccc
801   cccggtcgcc ccggccacac cggcaacccc ggccacgccc gttacccag
851   ctcccgctcc acccgcag ccggctccgg caccggcgcc atcgcctggg
901   ccccagccgg ttacaccggc cactcccggt ccgtctggtc cagcaacacc
951   gggcacccca ggggcgagc cggcgccgca cgtcaaaccc gcggcgttgg
1001  cggagcaacc tggtgtgccg ggccagcatg cgggcggggg gacgcagtcg
1051  gggcctgccc atgcggacga atccgccgcg tcggtgacgc cggctgcggc
1101  gtccggtgtc ccgggcgcac gggcggcggc cgccgcgccg agcggtaccg
1151  ccgtgggagc gggcgcgcgt tcgagcgtgg gtacggccgc ggcctcgggc
1201  gcggggtcgc atgctgccac tgggcgggcg ccggtggcta cctcggacaa
1251  ggcggcggca ccgagcacgc gggcggcctc ggcgcggacg gcacctcctg
1301  cccgcccgcc gtcgaccgat cacatcgaca aacccgatcg cagcgagtct
1351  gcagatgacg gtacgccggt gtcgatgatc ccggtgtcgg cggctcgggc
1401  ggcacgcgac gccgccactg cagctgccag cgcccgccag cgtggccgcg
1451  gtgatgcgct gcggttggcg cgacgcatcg cggcggcgct caacgcgtcc
1501  gacaacaacg cgggcgacta cgggttcttc tggatcaccg cggtgaccac
1551  cgacggttcc atcgtcgtgg ccaacagcta gggctggcc tacatacccg
1601  acgggatgga attgccgaat aaggtgtact tggccagcgc ggatcacgca
1651  atcccggttg acgaaattgc acgctgtgcc acctacccgg ttttggccgt
1701  gcaagcctgg gcggctttcc acgacatgac gctgcgggcg gtgatcggta
1751  ccgcggagca gttggccagt tcggatcccg gtgtggccaa gattgtgctg
1801  gagccagatg acattccgga gcggcaaa atgacgggcc ggtcgcggct
1851  ggaggtcgtc gaccctcgg cggcggctca gctggccgac actaccgatc
1901  agcgttgct cgacttgttg ccgccggcgc cggtggatgt caatccaccg
1951  ggcgatgagc ggcacatgct gtggttcgag ctgatgaagc ccatgaccag
2001  caccgctacc ggccgcgagg ccgctcatct gcgggcgttc cgggcctacg
2051  ctgcccactc acaggagatt gccctgcacc aagcgcacac tgcgactgac
2101  gcggccgtcc agcgtgtggc cgtcgcggac tggctgtact ggcaatacgt
2151  caccgggttg ctcgaccggg ccctggccgc cgcatgctga
```

FIG 2E

PROTEINS EXPRESSED BY MYCOBACTERIUM TUBERCULOSIS AND NOT BY BCG AND THEIR USE AS DIAGNOSTIC REAGENTS AND VACCINES

This application is a divisional of, and claims priority to, U.S. application Ser. No. 13/893,659, filed May 14, 2013, which is a divisional of, and claims priority to, U.S. application Ser. No. 13/198,108, filed Aug. 4, 2011, which is a continuation of, and claims priority to, U.S. application Ser. No. 12/503,717, filed Jul. 15, 2009 and now issued as U.S. Pat. No. 8,021,832, which is a continuation of, and claims priority to, U.S. application Ser. No. 11/677,502, filed Feb. 21, 2007, now U.S. Pat. No. 7,579,141, which is a divisional of, and claims priority to, U.S. application Ser. No. 10/009,383, filed Mar. 4, 2002 and now issued as U.S. Pat. No. 7,932,373, which claims priority to International Application No. PCT/US00/12257, filed May 4, 2000, which claims priority to U.S. Provisional Application Ser. No. 60/132,505, filed May 4, 1999, the disclosures of each of which are hereby incorporated by reference in their entireties.

BACKGROUND OF THE INVENTION

Tuberculosis infection continues to be a world-wide health problem. This situation has recently been greatly exacerbated by the emergence of multi-drug resistant strains of *M. tuberculosis* and the international AIDS epidemic. It has thus become increasingly important that effective vaccines against and reliable diagnostic reagents for *M. tuberculosis* be produced.

The disclosure of U.S. Pat. No. 6,087,163 is incorporated herein by reference in its entirety.

SUMMARY OF THE INVENTION

The invention is based on the inventor's discovery that a polypeptide encoded by an open reading frame (ORF) in the genome of *M. tuberculosis* that is absent from the genome of the Bacille Calmette Guerin (BCG) strain of *M. bovis* elicited a delayed-type hypersensitivity response in animals infected with *M. tuberculosis* but not in animals sensitized with BCG. Thus proteins encoded by ORFs present in the genome of *M. tuberculosis* but absent from the genome of BCG represent reagents that are useful in discriminating between *M. tuberculosis* and BCG and, in particular, for diagnostic methods (e.g., skin tests and in vitro assays for *M. tuberculosis*-specific antibodies and lymphocyte responsiveness) which discriminate between exposure of a subject to *M. tuberculosis* and vaccination with BCG. The invention features these polypeptides, functional segments thereof, DNA molecules encoding either the polypeptides or the functional segments, vectors containing the DNA molecules, cells transformed by the vectors, compositions containing one or more of any of the above polypeptides, functional segments, or DNA molecules, and a variety of diagnostic, therapeutic, and prophylactic (vaccine) methodologies utilizing the foregoing.

Specifically, the invention features an isolated DNA molecule containing a DNA sequence encoding a polypeptide with a first amino acid sequence that can be the amino acid sequence of the polypeptide MTBN1, MTBN2, MTBN3, MTBN4, MTBN5, MTBN6, MTBN7 or MTBN8, as depicted in FIGS. 1A and 1B, or a second amino acid sequence identical to the first amino acid sequence with conservative substitutions; the polypeptide has *Mycobacterium tuberculosis* specific antigenic and immunogenic properties. Also included in the invention is an isolated portion of the above DNA molecule. The portion of the DNA molecule encodes a segment of the polypeptide shorter than the full-length polypeptide, and the segment has *Mycobacterium tuberculosis* specific antigenic and immunogenic properties. Other embodiments of the invention are vectors containing the above DNA molecules and transcriptional and translational regulatory sequences operationally linked to the DNA sequence; the regulatory sequences allow for expression of the polypeptide or functional segment encoded by the DNA sequence in a cell. The invention encompasses cells (e.g., eukaryotic and prokaryotic cells) transformed with the above vectors.

The invention encompasses compositions containing any of the above vectors and a pharmaceutically acceptable diluent or filler. Other compositions (to be used, for example, as DNA vaccines) can contain at least two (e.g., three, four, five, six, seven, eight, nine, ten, twelve, fifteen, or twenty) DNA sequences, each encoding a polypeptide of the *Mycobacterium tuberculosis* complex or a functional segment thereof, with the DNA sequences being operationally linked to transcriptional and translational regulatory sequences which allow for expression of each of the polypeptides in a cell of a vertebrate. In such compositions, at least one (e.g., two, three, four, five, six, seven, or eight) of the DNA sequences is one of the above DNA molecules of the invention. The encoded polypeptides will preferably be those not encoded by the genome of cells of the BCG strain of *M. bovis*.

The invention also features an isolated polypeptide with a first amino acid sequence that can be the sequence of the polypeptide MTBN1, MTBN2, MTBN3, MTBN4, MTBN5, MTBN6, MTBN7 or MTBN8 as depicted in FIGS. 1A and 1B, or a second amino acid sequence identical to the first amino acid sequence with conservative substitutions. The polypeptide has *Mycobacterium tuberculosis* specific antigenic and immunogenic properties. Also included in the invention is an isolated segment of this polypeptide, the segment being shorter than the full-length polypeptide and having *Mycobacterium tuberculosis* specific antigenic and immunogenic properties. Other embodiments are compositions containing the polypeptide, or functional segment, and a pharmaceutically acceptable diluent or filler. Compositions of the invention can also contain at least two (e.g., three, four, five, six, seven, eight, nine, ten, twelve, fifteen, or twenty) polypeptides of the *Mycobacterium tuberculosis* complex, or functional segments thereof, with at least one of the at least two (e.g., two, three, four, five, six, seven, or eight) polypeptides having the sequence of one of the above described polypeptides of the invention. The polypeptides will preferably be those not encoded by the genome of cells of the BCG strain of *M. bovis*.

The invention also features methods of diagnosis. One embodiment is a method involving: (a) administration of one of the above polypeptide compositions to a subject suspected of having or being susceptible to *Mycobacterium tuberculosis* infection; and (b) detecting an immune response in the subject to the composition, as an indication that the subject has or is susceptible to *Mycobacterium tuberculosis* infection. An example of such a method is a skin test in which the test substance (e.g., compositions containing one or more of MTBN1-MTBN8) is injected intradermally into the subject and in which a skin delayed-type hypersensitivity response is tested for. Another embodiment is a method that involves: (a) providing a population of cells containing CD4 T lymphocytes from a subject; (b) providing a population of cells containing antigen presenting cells (APC) expressing a major histocompatibility complex (MHC) class II molecule expressed by the subject; (c) contacting the CD4 lymphocytes of (a) with the APC of (b) in the presence of one or more of the polypeptides, functional segments, and or polypeptide compositions of the invention; and (d) determining the ability of the CD4 lymphocytes to respond to the polypeptide, as an indication that the subject has or is susceptible to *Mycobacterium tuberculosis* infection. Another diagnostic method of the invention involves: (a) contacting a polypeptide, a functional segment, or a polypeptide/functional segment composition of the invention with a bodily fluid of a subject; (b) detecting the presence of binding of antibody to the polypeptide, functional segment, or polypeptide/functional segment composition, as an indication that the subject has or is susceptible to *Mycobacterium tuberculosis* infection.

Also encompassed by the invention are methods of vaccination. These methods involve administration of any of the above polypeptides, functional segments, or DNA compositions to a subject. The compositions can be administered alone or with one or more of the other compositions.

As used herein, an "isolated DNA molecule" is a DNA which is one or both of: not immediately contiguous with one or both of the coding sequences with which it is immediately contiguous (i.e., one at the 5' end and one at the 3' end) in the naturally-occurring genome of the organism from which the DNA is derived; or which is substantially free of DNA sequence with which it occurs in the organism from which the DNA is derived. The term includes, for example, a recombinant DNA which incorporated into a vector, e.g., into an autonomously replicating plasmid or virus, or into the genomic DNA of a prokaryote or eukaryote, or which exists as a separate molecule (e.g., a cDNA or a genomic fragment produced by PCR or restriction endonuclease treatment) independent of other DNA sequences. Isolated DNA also includes a recombinant DNA which is part of a hybrid DNA encoding additional *M. tuberculosis* polypeptide sequences.

"DNA molecules" include cDNA, genomic DNA, and synthetic (e.g., chemically synthesized) DNA. Where single-stranded, the DNA molecule may be a sense strand or an antisense strand.

An "isolated polypeptide" of the invention is a polypeptide which either has no naturally-occurring counterpart, or has been separated or purified from components which naturally accompany it, e.g., in *M. tuberculosis* bacteria. Typically, the polypeptide is considered "isolated" when it is at least 70%, by dry weight, free from the proteins and naturally-occurring organic molecules with which it is naturally associated.

Preferably, a preparation of a polypeptide of the invention is at least 80%, more preferably at least 90%, and most preferably at least 99%, by dry weight, the peptide of the invention. Since a polypeptide that is chemically synthesized is, by its nature, separated from the components that naturally accompany it, the synthetic polypeptide is "isolated."

An isolated polypeptide of the invention can be obtained, for example, by extraction from a natural source (e.g., *M. tuberculosis* bacteria); by expression of a recombinant nucleic acid encoding the polypeptide; or by chemical synthesis. A polypeptide that is produced in a cellular system different from the source from which it naturally originates is "isolated," because it will be separated from components which naturally accompany it. The extent of isolation or purity can be measured by any appropriate method, e.g., column chromatography, polyacrylamide gel electrophoresis, or HPLC analysis.

The polypeptides may contain a primary amino acid sequence that has been modified from those disclosed herein. Preferably these modifications consist of conservative amino acid substitutions. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

The terms "protein" and "polypeptide" are used herein to describe any chain of amino acids, regardless of length or post-translational modification (for example, glycosylation or phosphorylation). Thus, the term "*Mycobacterium tuberculosis* polypeptide" includes full-length, naturally occurring *Mycobacterium tuberculosis* protein, as well a recombinantly or synthetically produced polypeptide that corresponds to a full-length naturally occurring *Mycobacterium tuberculosis* protein or to particular domains or portions of a naturally occurring protein. The term also encompasses a mature *Mycobacterium tuberculosis* polypeptide which has an added amino-terminal methionine (useful for expression in prokaryotic cells) or any short amino acid sequences useful for protein purification by affinity chromatography, e.g., polyhistidine for purification by metal chelate chromatography.

As used herein, "immunogenic" means capable of activating a primary or memory immune response. Immune responses include responses of CD4+ and CD8+ T lymphocytes and B-lymphocytes. In the case of T lymphocytes, such responses can be proliferative, and/or cytokine (e.g., interleukin (IL)-2, IL-3, IL-4, IL-5, IL-6, IL-12, IL-13, IL-15, tumor necrosis factor-a (TNF-a), or interferon-y (IFN-y))-producing, or they can result in generation of cytotoxic T-lymphocytes (CTL). B-lymphocyte responses can be those resulting in antibody production by the responding B lymphocytes.

As used herein, "antigenic" means capable of being recognized by either antibody molecules or antigen-specific T cell receptors (TCR) on activated effector T cells (e.g., cytokine-producing T cells or CTL).

Thus, polypeptides that have "*Mycobacterium tuberculosis* specific antigenic properties" are polypeptides that: (a) can be recognized by and bind to antibodies elicited in response to *Mycobacterium tuberculosis* organisms or wild-type *Mycobacterium tuberculosis* molecules (e.g., polypeptides); or (b) contain subsequences which, subsequent to processing of the polypeptide by appropriate antigen presenting cells (APC) and bound to appropriate major histocompatibility complex (MHC) molecules, are recognized by and bind to TCR on effector T cells elicited in response to *Mycobacterium tuberculosis* organisms or wild-type *Mycobacterium tuberculosis* molecules (e.g., polypeptides).

As used herein, polypeptides that have "*Mycobacterium tuberculosis* specific immunogenic properties" are polypeptides that: (a) can elicit the production of antibodies that recognize and bind to *Mycobacterium tuberculosis* organisms or wild-type *Mycobacterium tuberculosis* molecules (e.g., polypeptides); or (b) contain subsequences which, subsequent to processing of the polypeptide by appropriate antigen presenting cells (APC) and bound to appropriate major histocompatibility complex (MHC) molecules on the surface of the APC, activate T cells with TCR that recognize and bind to peptide fragments derived by processing by APC of *Mycobacterium tuberculosis* organisms or wild-type *Mycobacterium tuberculosis* molecules (e.g., polypeptides) and bound to MHC molecules on the surface of the APC. The immune responses elicited in response to the immunogenic polypeptides are preferably protective. As used herein, "protective" means preventing establishment of an infection or onset of a disease or lessening the severity of a disease existing in a subject. "Preventing" can include delaying onset, as well as partially or completely blocking progress of the disease.

As used herein, a "functional segment of a *Mycobacterium tuberculosis* polypeptide" is a segment of the polypeptide that has *Mycobacterium tuberculosis* specific antigenic and immunogenic properties.

Where a polypeptide, functional segment of a polypeptide, or a mixture of polypeptides and/or functional segments have been administered (e.g., by intradermal injection) to a subject for the purpose of testing for a *M. tuberculosis* infection or susceptibility to such an infection, "detecting an immune response" means examining the subject for signs of an immunological reaction to the administered material, e.g., reddening or swelling of the skin at the site of an intradermal injection. Where the subject has antibodies to the administered material, the response will generally be rapid, e.g., 1 minute to 24 hours. On the other hand, a memory or activated T cell reaction of pre-immunized T lymphocytes in the subject is generally slower, appearing only after 24 hours and being maximal at 24-96 hours.

As used herein, a "subject" can be a human subject or a non-human mammal such as a non-human primate, a horse, a bovine animal, a pig, a sheep, a goat, a dog, a cat, a rabbit, a guinea pig, a hamster, a rat, or a mouse.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the present invention. Unless otherwise indicated, these materials and methods are illustrative only and are not intended to be limiting.

All publications, patent applications, patents and other references mentioned herein are illustrative only and not intended to be limiting.

Other features and advantages of the invention, e.g., methods of diagnosing *M. tuberculosis* infection, will be apparent from the following description, from the drawings and from the claims.

BRIEF DESCRIPTION OF THE DRAWINGS

FIGS. 1A and 1B are a depiction of the amino acid sequences of *M. tuberculosis* polypeptides MTBN1-MTBN8 (SEQ ID NOS:1-8, respectively).

FIGS. 2A-2E are a depiction of the nucleotide sequences of the coding regions (mtbn1-mtbn8) encoding MTBN1-MTBN8 (SEQ ID NOS:9-16, respectively).

FIG. 3 is a bar graph showing the delayed-type hypersensitivity responses induced by intradermal injection of 3 different test reagents in female guinea pigs that had been either infected with *M. tuberculosis* cells or sensitized with BCG or *M. avium* cells.

DETAILED DESCRIPTION

The genome of *M. tuberculosis* [Cole et al. (1998) Nature 393: 537-544] contains open reading frames (ORFs) that have been deleted from the avirulent BCG strain.

The polypeptides encoded by these ORFs are designated herein "*M. tuberculosis* BCG Negative" polypeptides ("MTBN") and the ORFs are designated "mtbn." The invention is based on the discovery that a MTBN polypeptide (MTBN4) elicited a skin response in animals infected with *M. tuberculosis*, but not in animals sensitized to either BCG or *M. avium*, a non-*M. tuberculosis*-complex strain of mycobacteria (see Example 1 below). These findings indicate that MTBN (e.g., MTBN1-MTBN8) can be used in diagnostic tests that discriminate infection of a subject by *M. tuberculosis* from exposure to both mycobacteria other than the *M. tuberculosis*-complex and BCG. The *M. tuberculosis*-complex includes *M. tuberculosis, M. bovis, M. microti*, and *M. africanum*. Thus they can be used to discriminate subjects exposed to *M. tuberculosis*, and thus potentially having or being in danger of having tuberculosis, from subjects that have been vaccinated with BCG, the most widely used tuberculosis vaccine. Diagnostic assays that are capable of such discrimination represent a major advance that will greatly reduce wasted effort and consequent costs resulting from further diagnostic tests and/or therapeutic procedures in subjects that have given positive results in less discriminatory diagnostic tests.

Furthermore, the results in Example 1 show that MTBN4, as expressed by whole viable *M. tuberculosis* organisms, is capable of inducing a strong immune response in subjects infected with the organisms and thus has the potential to be a vaccine.

The MTBN polypeptides of the invention include, for example, polypeptides encoded within the RD1, RD2, and RD3 regions of the *M. tuberculosis* genome [Mahairas et al. (1996) J. Bacteriol. 178: 1274-1282]. Of particular interest are polypeptides encoded by ORFs within the RD1 region of the *M. tuberculosis* genome. However, the invention is not restricted to the RD1, RD2, and RD3 region encoded polypeptides and includes any polypeptides encoded by ORFs contained in the genome of one or more members of the *M. tuberculosis* genome and not contained in the genome of BCG. The amino acid sequences of MTBN1-MTBN8 are shown in FIGS. 1A and 1B and the nucleotide sequences of mtbn1-mtbn8 are shown in FIGS. 2A-2E.

The invention encompasses: (a) isolated DNA molecules containing mtbn sequences (e.g., mtbn1-mtbn8) encoding MTBN polypeptides (e.g., MTBN1-MTBN8) and isolated portions of such DNA molecules that encode polypeptide segments having antigenic and immunogenic properties (i.e., functional segments); (b) the MTBN polypeptides themselves (e.g., MTBN1-MTBN8) and functional segments of them; (c) antibodies (including antigen binding fragments, e.g., F(ab') 2, Fab, Fv, and single chain Fv fragments of such antibodies) that bind to the MTBN polypeptides (e.g., MTBN1-MTBN8) and functional segments; (d) nucleic acid molecules (e.g., vectors) containing and capable of expressing one or more of the mtbn (e.g., mtbn1-mtbn8) sequences and portions of DNA molecules; (e) cells (e.g., bacterial, yeast, insect, or mammalian cells) transformed by such vectors; (f) compositions containing vectors encoding one or more *M. tuberculosis* polypeptides (or functional segments) including both the MTBN (e.g., MTBN1-MTBN8) polypeptides (or functional segments thereof) and previously described *M. tuberculosis* polypeptides such as ESAT-6, 14 kDa antigen, MPT63, 19 kDa antigen, MPT64, MPT51, MTC28, 38 kDa antigen, 45/47 kDa antigen, MPB70, Ag85 complex, MPT53, and KatG (see also U.S. Pat. No. 6,087, 163); (g) compositions containing one or more *M. tuberculosis* polypeptides (or functional segments), including both the polypeptides of the invention and previously described *M. tuberculosis* polypeptides such as those described above; (h) compositions containing one or more of the antibodies described in (c); (i) methods of diagnosis involving either (1) administration (e.g., intradermal injection) of any of the above polypeptide compositions to a subject suspected of having or being susceptible to *M. tuberculosis* infection, (2) in vitro testing of lymphocytes (B-lymphocytes, CD4 T lymphocytes, and CD8 T lymphocytes) from such a subject for responsiveness (e.g., by measuring cell proliferation, antibody production, cytokine production, or CTL activity) to any of the above polypeptide compositions, (3) testing of a bodily fluid (e.g., blood, saliva, plasma, serum, urine, or semen or a lavage such as a bronchoalveolar lavage, a vaginal lavage, or lower gastrointestinal lavage) for antibodies to the MTBN polypeptides (e.g., MTBN1-MTBN8) or functional segments thereof, or the above-described polypeptide compositions; (4) testing of a bodily fluid (e.g., as above) for the presence of *M. tuberculosis*, MTBN (e.g., MTBN1-MTBN8) polypeptides or functional segments thereof, or the above-described polypeptide compositions in assays using the antibodies described in (c); and (5) testing of a tissue (e.g., lung or bronchial tissue) or a body fluid (e.g., as above) for the presence of nucleic acid molecules (e.g., DNA or RNA) encoding MTBN polypeptides (e.g., MTBN1-MTBN8) (or portions of such a nucleic acid molecules) using nucleic acid probes or primers having nucleotide sequences of the nucleic molecules, portions of the nucleic molecules, or the complements of such molecules; and (j) methods of vaccination involving administration to a subject of the compositions of either (f), (g), (h) or a combination of any two or even all 3 compositions.

With respect to diagnosis, purified MTBN proteins, functional segments of such proteins, or mixtures of proteins and/or the functional fragments have the above-described advantages of discriminating infection by *M. tuberculosis* from either infection by other bacteria, and in particular, non-pathogenic mycobacteria, or from exposure (by, for example, vaccination) to BCG.

Furthermore, compositions containing the proteins, functional segments of the proteins, or mixtures of the proteins and/or the functional segments allows for improved quality control since "batch-to-batch" variability is greatly reduced in comparison to complex mixtures such as purified protein derivative (PPD) of tuberculin.

The use of the above-described polypeptide and nucleic acid reagents for vaccination also provides for highly specific and effective immunization. Since the virulent *M. tuberculosis* polypeptides encoded by genes absent from avirulent BCG are likely to be mediators of virulence, immunity directed to them can be especially potent in terms of protective capacity. Where vaccination is performed with nucleic acids both in vivo and ex vivo methods can be used. In vivo methods involve administration of the nucleic acids themselves to the subject and ex vivo methods involve obtaining cells (e.g., bone marrow cells or fibroblasts) from the subject, transducing the cells with the nucleic acids, preferably selecting or enriching for successfully transduced cells, and administering the transduced cells to the subject. Alternatively, the cells that are transduced and administered to the subject can be derived from another subject. Methods of vaccination and diagnosis are described in greater detail in U.S. Pat. No. 6,087,163, the disclosure of which is incorporated herein by reference in its entirety.

The following example is meant to illustrate, not limit the invention.

Example 1

MTBN4 Elicits a Specific Skin Reaction in Guinea Pigs Infected with *M. tuberculosis*

Four groups of outbred female guinea pigs (18 per group) were used to test the usefulness of the MTBN4 polypeptide as a *M. tuberculosis*-specific diagnostic reagent. The four groups were treated as follows.

Group 1 animals were infected by aerosol with approximately 100 *M. tuberculosis* strain H37Rv cells.

Group 2 animals were sensitized intradermally with 106 live *M. bovis* BCG Japanese cells.

Group 3 animals were sensitized intradermally with 106 live *M. avium* cells.

Group 4 animals were mock-sensitized by intradermal injection with saline.

Seven weeks after infection or sensitization, the animals were injected intradermally with 1 μg of PPD (6 animals from each group), 2 μg of purified recombinant MPT64 (6 animals from each group), or 2 μg of MTBN4 (6 animals from each group). The diameter of the resulting erythema was measured 24 hours later. Data are expressed as mean diameter of erythema (in mm) and standard deviations are indicated (FIG. 3).

No erythema was detected in the group 4 animals with any test substance and thus no data are shown for this group. On the other hand, group 1 animals (solid bars) showed a significant response with all three test substances. Group 2 animals (open bars) showed a significant response to PPD and MPT64 but not MTBN4.

Group 3 animals showed a significant response to PPD only (hatched bars).

Thus, PPD which contains antigenic/immunogenic molecules common to the *M. tuberculosis*-complex as well as other mycobacterial strains, gave the least discriminatory results in that it induced responses in animals infected with or sensitized to mycobacteria of the *M. tuberculosis*-complex (*M. tuberculosis* and BCG) as well as another non-pathogenic mycobacterium (*M. avium*).

While MPT64, which is encoded and expressed by both *M. tuberculosis* and BCG, did not elicit a response in animals infected with *M. avium*, it did elicit responses in both the *M. tuberculosis* infected and the BCG sensitized animals. Finally, MTBN4 elicited a response in only the *M. tuberculosis* animals. Thus it induced the most specific response and, most importantly, allowed for discrimination between animals infected with *M. tuberculosis* and those sensitized to BCG.

Although the invention has been described with reference to the presently preferred embodiment, it should be understood that various modifications can be made without departing from the spirit of the invention. Accordingly, the invention is limited only by the following claims.

What is claimed:

1. A method of in vitro diagnosis that discriminates between infection by *Mycobacterium tuberculosis*-complex and vaccination by Bacille Calmette Guerin (BCG) strain of *Mycobacterium bovis* comprising:
   providing a population of cells comprising CD4 T lymphocytes from a subject and antigen presenting cells (APC) expressing at least one major histocompatibility complex (MHC) class II molecule expressed by said subject;
   contacting cells of the population with at least two different antigens, wherein the antigens are isolated polypeptides of the *Mycobacterium tuberculosis*-complex that are not encoded by BCG, including at least one isolated polypeptide selected from the group consisting of (i) a first amino acid sequence comprising the sequence of MTBN4 (SEQ ID NO: 4), (ii) a second amino acid sequence that is an antigenic segment of MTBN4 and (iii) a third amino acid sequence that is identical to said first or second amino acid sequence but that has conservative substitutions and that retains *Mycobacterium tuberculosis*-complex specific antigenic properties; and
   determining whether or not there has been an immune response to said at least two antigens.

2. The method of claim 1, wherein said at least one isolated polypeptide comprises said first or second amino acid sequence.

3. The method of claim 1, wherein the step of contacting is contacting said cells with a composition containing said at least two antigens.

4. The method of claim 3, wherein the determining step comprises testing for production of at least one cytokine.

5. The method of claim 4, wherein the at least one cytokine includes interferon-γ (IFN-γ).

6. The method of claim 1, wherein the determining step comprises testing for production of at least one cytokine.

7. The method of claim 6, wherein at least one cytokine includes interferon-γ (IFN-γ).

8. The method of claim 1, wherein the isolated polypeptides of the *Mycobacterium tuberculosis*-complex are encoded within the RD1, RD2, and RD3 regions.

* * * * *

SEQUENCE LISTING

```
<160> NUMBER OF SEQ ID NOS: 16

<210> SEQ ID NO 1
<211> LENGTH: 591
<212> TYPE: PRT
<213> ORGANISM: Mycobacterium tuberculosis
```

```
<400> SEQUENCE: 1

Met Thr Ala Glu Pro Glu Val Arg Thr Leu Arg Glu Val Val Leu Asp
 1               5                  10                  15

Gln Leu Gly Thr Ala Glu Ser Arg Ala Tyr Lys Met Trp Leu Pro Pro
             20                  25                  30

Leu Thr Asn Pro Val Pro Leu Asn Glu Leu Ile Ala Arg Asp Arg Arg
         35                  40                  45

Gln Pro Leu Arg Phe Ala Leu Gly Ile Met Asp Glu Pro Arg Arg His
     50                  55                  60

Leu Gln Asp Val Trp Gly Val Asp Val Ser Gly Ala Gly Gly Asn Ile
 65                  70                  75                  80

Gly Ile Gly Gly Ala Pro Gln Thr Gly Lys Ser Thr Leu Leu Gln Thr
                 85                  90                  95

Met Val Met Ser Ala Ala Ala Thr His Ser Pro Arg Asn Val Gln Phe
             100                 105                 110

Tyr Cys Ile Asp Leu Gly Gly Gly Leu Ile Tyr Leu Glu Asn Leu
         115                 120                 125

Pro His Val Gly Gly Val Ala Asn Arg Ser Glu Pro Asp Lys Val Asn
     130                 135                 140

Arg Val Val Ala Glu Met Gln Ala Val Met Arg Gln Arg Glu Thr Thr
145                 150                 155                 160

Phe Lys Glu His Arg Val Gly Ser Ile Gly Met Tyr Arg Gln Leu Arg
                 165                 170                 175

Asp Asp Pro Ser Gln Pro Val Ala Ser Asp Pro Tyr Gly Asp Val Phe
             180                 185                 190

Leu Ile Ile Asp Gly Trp Pro Gly Phe Val Gly Glu Phe Pro Asp Leu
         195                 200                 205

Glu Gly Gln Val Gln Asp Leu Ala Ala Gln Gly Leu Ala Phe Gly Val
     210                 215                 220

His Val Ile Ile Ser Thr Pro Arg Trp Thr Glu Leu Lys Ser Arg Val
225                 230                 235                 240

Arg Asp Tyr Leu Gly Thr Lys Ile Glu Phe Arg Leu Gly Asp Val Asn
                 245                 250                 255

Glu Thr Gln Ile Asp Arg Ile Thr Arg Glu Ile Pro Ala Asn Arg Pro
             260                 265                 270

Gly Arg Ala Val Ser Met Glu Lys His His Leu Met Ile Gly Val Pro
         275                 280                 285

Arg Phe Asp Gly Val His Ser Ala Asp Asn Leu Val Glu Ala Ile Thr
     290                 295                 300

Ala Gly Val Thr Gln Ile Ala Ser Gln His Thr Glu Gln Ala Pro Pro
305                 310                 315                 320

Val Arg Val Leu Pro Glu Arg Ile His Leu His Glu Leu Asp Pro Asn
                 325                 330                 335

Pro Pro Gly Pro Glu Ser Asp Tyr Arg Thr Arg Trp Glu Ile Pro Ile
             340                 345                 350

Gly Leu Arg Glu Thr Asp Leu Thr Pro Ala His Cys His Met His Thr
         355                 360                 365

Asn Pro His Leu Leu Ile Phe Gly Ala Ala Lys Ser Gly Lys Thr Thr
     370                 375                 380

Ile Ala His Ala Ile Ala Arg Ala Ile Cys Ala Arg Asn Ser Pro Gln
385                 390                 395                 400

Gln Val Arg Phe Met Leu Ala Asp Tyr Arg Ser Gly Leu Leu Asp Ala
                 405                 410                 415
```

```
Val Pro Asp Thr His Leu Leu Gly Ala Gly Ala Ile Asn Arg Asn Ser
            420                 425                 430

Ala Ser Leu Asp Glu Ala Val Gln Ala Leu Ala Val Asn Leu Lys Lys
            435                 440                 445

Arg Leu Pro Pro Thr Asp Leu Thr Thr Ala Gln Leu Arg Ser Arg Ser
450                 455                 460

Trp Trp Ser Gly Phe Asp Val Val Leu Leu Val Asp Asp Trp His Met
465                 470                 475                 480

Ile Val Gly Ala Ala Gly Gly Met Pro Pro Met Ala Pro Leu Ala Pro
                485                 490                 495

Leu Leu Pro Ala Ala Asp Ile Gly Leu His Ile Ile Val Thr Cys
            500                 505                 510

Gln Met Ser Gln Ala Tyr Lys Ala Thr Met Asp Lys Phe Val Gly Ala
            515                 520                 525

Ala Phe Gly Ser Gly Ala Pro Thr Met Phe Leu Ser Gly Glu Lys Gln
            530                 535                 540

Glu Phe Pro Ser Ser Glu Phe Lys Val Lys Arg Arg Pro Pro Gly Gln
545                 550                 555                 560

Ala Phe Leu Val Ser Pro Asp Gly Lys Glu Val Ile Gln Ala Pro Tyr
                565                 570                 575

Ile Glu Pro Pro Glu Glu Val Phe Ala Ala Pro Pro Ser Ala Gly
            580                 585                 590

<210> SEQ ID NO 2
<211> LENGTH: 99
<212> TYPE: PRT
<213> ORGANISM: Mycobacterium tuberculosis

<400> SEQUENCE: 2

Met Glu Lys Met Ser His Asp Pro Ile Ala Ala Asp Ile Gly Thr Gln
1               5                   10                  15

Val Ser Asp Asn Ala Leu His Gly Val Thr Ala Gly Ser Thr Ala Leu
                20                  25                  30

Thr Ser Val Thr Gly Leu Val Pro Ala Gly Ala Asp Glu Val Ser Ala
            35                  40                  45

Gln Ala Ala Thr Ala Phe Thr Ser Glu Gly Ile Gln Leu Leu Ala Ser
        50                  55                  60

Asn Ala Ser Ala Gln Asp Gln Leu His Arg Ala Gly Glu Ala Val Gln
65                  70                  75                  80

Asp Val Ala Arg Thr Tyr Ser Gln Ile Asp Asp Gly Ala Ala Gly Val
                85                  90                  95

Phe Ala Glu

<210> SEQ ID NO 3
<211> LENGTH: 368
<212> TYPE: PRT
<213> ORGANISM: Mycobacterium tuberculosis

<400> SEQUENCE: 3

Met Leu Trp His Ala Met Pro Pro Glu Leu Asn Thr Ala Arg Leu Met
1               5                   10                  15

Ala Gly Ala Gly Pro Ala Pro Met Leu Ala Ala Ala Gly Trp Gln
                20                  25                  30

Thr Leu Ser Ala Ala Leu Asp Ala Gln Ala Val Glu Leu Thr Ala Arg
            35                  40                  45
```

```
Leu Asn Ser Leu Gly Glu Ala Trp Thr Gly Gly Ser Asp Lys Ala
 50                  55                  60

Leu Ala Ala Ala Thr Pro Met Val Val Trp Leu Gln Thr Ala Ser Thr
 65                  70                  75                  80

Gln Ala Lys Thr Arg Ala Met Gln Ala Thr Ala Gln Ala Ala Tyr
             85                  90                  95

Thr Gln Ala Met Ala Thr Thr Pro Ser Leu Pro Glu Ile Ala Ala Asn
                100                 105                 110

His Ile Thr Gln Ala Val Leu Thr Ala Thr Asn Phe Phe Gly Ile Asn
            115                 120                 125

Thr Ile Pro Ile Ala Leu Thr Glu Met Asp Tyr Phe Ile Arg Met Trp
130                 135                 140

Asn Gln Ala Ala Leu Ala Met Glu Val Tyr Gln Ala Glu Thr Ala Val
145                 150                 155                 160

Asn Thr Leu Phe Glu Lys Leu Glu Pro Met Ala Ser Ile Leu Asp Pro
                165                 170                 175

Gly Ala Ser Gln Ser Thr Thr Asn Pro Ile Phe Gly Met Pro Ser Pro
            180                 185                 190

Gly Ser Ser Thr Pro Val Gly Gln Leu Pro Pro Ala Ala Thr Gln Thr
            195                 200                 205

Leu Gly Gln Leu Gly Glu Met Ser Gly Pro Met Gln Gln Leu Thr Gln
210                 215                 220

Pro Leu Gln Gln Val Thr Ser Leu Phe Ser Gln Val Gly Gly Thr Gly
225                 230                 235                 240

Gly Gly Asn Pro Ala Asp Glu Glu Ala Ala Gln Met Gly Leu Leu Gly
                245                 250                 255

Thr Ser Pro Leu Ser Asn His Pro Leu Ala Gly Gly Ser Gly Pro Ser
            260                 265                 270

Ala Gly Ala Gly Leu Leu Arg Ala Glu Ser Leu Pro Gly Ala Gly Gly
            275                 280                 285

Ser Leu Thr Arg Thr Pro Leu Met Ser Gln Leu Ile Glu Lys Pro Val
290                 295                 300

Ala Pro Ser Val Met Pro Ala Ala Ala Gly Ser Ser Ala Thr Gly
305                 310                 315                 320

Gly Ala Ala Pro Val Gly Ala Gly Ala Met Gly Gln Gly Ala Gln Ser
                325                 330                 335

Gly Gly Ser Thr Arg Pro Gly Leu Val Ala Pro Ala Pro Leu Ala Gln
            340                 345                 350

Glu Arg Glu Glu Asp Asp Glu Asp Asp Trp Asp Glu Asp Asp Trp
            355                 360                 365

<210> SEQ ID NO 4
<211> LENGTH: 100
<212> TYPE: PRT
<213> ORGANISM: Mycobacterium tuberculosis

<400> SEQUENCE: 4

Met Ala Glu Met Lys Thr Asp Ala Ala Thr Leu Ala Gln Glu Ala Gly
  1               5                  10                  15

Asn Phe Glu Arg Ile Ser Gly Asp Leu Lys Thr Gln Ile Asp Gln Val
             20                  25                  30

Glu Ser Thr Ala Gly Ser Leu Gln Gly Gln Trp Arg Gly Ala Ala Gly
         35                  40                  45

Thr Ala Ala Gln Ala Ala Val Val Arg Phe Gln Glu Ala Ala Asn Lys
 50                  55                  60
```

```
Gln Lys Gln Glu Leu Asp Glu Ile Ser Thr Asn Ile Arg Gln Ala Gly
 65                  70                  75                  80

Val Gln Tyr Ser Arg Ala Asp Glu Glu Gln Gln Ala Leu Ser Ser
                 85                  90                  95

Gln Met Gly Phe
            100

<210> SEQ ID NO 5
<211> LENGTH: 666
<212> TYPE: PRT
<213> ORGANISM: Mycobacterium tuberculosis

<400> SEQUENCE: 5

Met Ala Ala Asp Tyr Asp Lys Leu Phe Arg Pro His Glu Gly Met Glu
  1               5                  10                  15

Ala Pro Asp Asp Met Ala Ala Gln Pro Phe Phe Asp Pro Ser Ala Ser
                 20                  25                  30

Phe Pro Pro Ala Pro Ala Ser Ala Asn Leu Pro Lys Pro Asn Gly Gln
             35                  40                  45

Thr Pro Pro Pro Thr Ser Asp Asp Leu Ser Glu Arg Phe Val Ser Ala
 50                  55                  60

Pro Pro Pro Pro Pro Pro Pro Pro Pro Pro Pro Pro Thr Pro Met
 65                  70                  75                  80

Pro Ile Ala Ala Gly Glu Pro Pro Ser Pro Glu Pro Ala Ala Ser Lys
                 85                  90                  95

Pro Pro Thr Pro Pro Met Pro Ile Ala Gly Pro Glu Pro Ala Pro Pro
                100                 105                 110

Lys Pro Pro Thr Pro Pro Met Pro Ile Ala Gly Pro Glu Pro Ala Pro
             115                 120                 125

Pro Lys Pro Pro Thr Pro Pro Met Pro Ile Ala Gly Pro Ala Pro Thr
130                 135                 140

Pro Thr Glu Ser Gln Leu Ala Pro Pro Arg Pro Pro Thr Pro Gln Thr
145                 150                 155                 160

Pro Thr Gly Ala Pro Gln Gln Pro Glu Ser Pro Ala Pro His Val Pro
                165                 170                 175

Ser His Gly Pro His Gln Pro Arg Arg Thr Ala Pro Ala Pro Pro Trp
            180                 185                 190

Ala Lys Met Pro Ile Gly Glu Pro Pro Ala Pro Ser Arg Pro Ser
            195                 200                 205

Ala Ser Pro Ala Glu Pro Pro Thr Arg Pro Ala Pro Gln His Ser Arg
210                 215                 220

Arg Ala Arg Arg Gly His Arg Tyr Arg Thr Asp Thr Glu Arg Asn Val
225                 230                 235                 240

Gly Lys Val Ala Thr Gly Pro Ser Ile Gln Ala Arg Leu Arg Ala Glu
                245                 250                 255

Glu Ala Ser Gly Ala Gln Leu Ala Pro Gly Thr Glu Pro Ser Pro Ala
            260                 265                 270

Pro Leu Gly Gln Pro Arg Ser Tyr Leu Ala Pro Pro Thr Arg Pro Ala
            275                 280                 285

Pro Thr Glu Pro Pro Pro Ser Pro Ser Pro Gln Arg Asn Ser Gly Arg
            290                 295                 300

Arg Ala Glu Arg Arg Val His Pro Asp Leu Ala Ala Gln His Ala Ala
305                 310                 315                 320

Ala Gln Pro Asp Ser Ile Thr Ala Ala Thr Thr Gly Gly Arg Arg Arg
```

```
            325                 330                 335
Lys Arg Ala Ala Pro Asp Leu Asp Ala Thr Gln Lys Ser Leu Arg Pro
            340                 345                 350

Ala Ala Lys Gly Pro Lys Val Lys Val Lys Pro Gln Lys Pro Lys
        355                 360                 365

Ala Thr Lys Pro Pro Lys Val Ser Gln Arg Gly Trp Arg His Trp
        370                 375                 380

Val His Ala Leu Thr Arg Ile Asn Leu Gly Leu Ser Pro Asp Glu Lys
385                 390                 395                 400

Tyr Glu Leu Asp Leu His Ala Arg Val Arg Arg Asn Pro Arg Gly Ser
                405                 410                 415

Tyr Gln Ile Ala Val Val Gly Leu Lys Gly Gly Ala Gly Lys Thr Thr
                420                 425                 430

Leu Thr Ala Ala Leu Gly Ser Thr Leu Ala Gln Val Arg Ala Asp Arg
            435                 440                 445

Ile Leu Ala Leu Asp Ala Asp Pro Gly Ala Gly Asn Leu Ala Asp Arg
450                 455                 460

Val Gly Arg Gln Ser Gly Ala Thr Ile Ala Asp Val Leu Ala Glu Lys
465                 470                 475                 480

Glu Leu Ser His Tyr Asn Asp Ile Arg Ala His Thr Ser Val Asn Ala
                485                 490                 495

Val Asn Leu Glu Val Leu Pro Ala Pro Glu Tyr Ser Ser Ala Gln Arg
            500                 505                 510

Ala Leu Ser Asp Ala Asp Trp His Phe Ile Ala Asp Pro Ala Ser Arg
            515                 520                 525

Phe Tyr Asn Leu Val Leu Ala Asp Cys Gly Ala Gly Phe Phe Asp Pro
        530                 535                 540

Leu Thr Arg Gly Val Leu Ser Thr Val Ser Gly Val Val Val Val Ala
545                 550                 555                 560

Ser Val Ser Ile Asp Gly Ala Gln Gln Ala Ser Val Ala Leu Asp Trp
                565                 570                 575

Leu Arg Asn Asn Gly Tyr Gln Asp Leu Ala Ser Arg Ala Cys Val Val
            580                 585                 590

Ile Asn His Ile Met Pro Gly Glu Pro Asn Val Ala Val Lys Asp Leu
        595                 600                 605

Val Arg His Phe Glu Gln Gln Val Gln Pro Gly Arg Val Val Val Met
        610                 615                 620

Pro Trp Asp Arg His Ile Ala Ala Gly Thr Glu Ile Ser Leu Asp Leu
625                 630                 635                 640

Leu Asp Pro Ile Tyr Lys Arg Lys Val Leu Glu Leu Ala Ala Ala Leu
                645                 650                 655

Ser Asp Asp Phe Glu Arg Ala Gly Arg Arg
            660                 665

<210> SEQ ID NO 6
<211> LENGTH: 511
<212> TYPE: PRT
<213> ORGANISM: Mycobacterium tuberculosis

<400> SEQUENCE: 6

Leu Ser Ala Pro Ala Val Ala Ala Gly Pro Thr Ala Ala Gly Ala Thr
1               5                   10                  15

Ala Ala Arg Pro Ala Thr Thr Arg Val Thr Ile Leu Thr Gly Arg Arg
            20                  25                  30
```

```
Met Thr Asp Leu Val Leu Pro Ala Val Pro Met Glu Thr Tyr Ile
         35                  40                  45

Asp Asp Thr Val Ala Val Leu Ser Glu Val Leu Glu Asp Thr Pro Ala
 50                  55                  60

Asp Val Leu Gly Gly Phe Asp Phe Thr Ala Gln Gly Val Trp Ala Phe
 65                  70                  75                  80

Ala Arg Pro Gly Ser Pro Leu Lys Leu Asp Gln Ser Leu Asp Asp
                 85                  90                  95

Ala Gly Val Val Asp Gly Ser Leu Leu Thr Leu Val Ser Val Ser Arg
                100                 105                 110

Thr Glu Arg Tyr Arg Pro Leu Val Glu Asp Val Ile Asp Ala Ile Ala
             115                 120                 125

Val Leu Asp Glu Ser Pro Glu Phe Asp Arg Thr Ala Leu Asn Arg Phe
 130                 135                 140

Val Gly Ala Ala Ile Pro Leu Leu Thr Ala Pro Val Ile Gly Met Ala
 145                 150                 155                 160

Met Arg Ala Trp Trp Glu Thr Gly Arg Ser Leu Trp Trp Pro Leu Ala
                 165                 170                 175

Ile Gly Ile Leu Gly Ile Ala Val Leu Val Gly Ser Phe Val Ala Asn
             180                 185                 190

Arg Phe Tyr Gln Ser Gly His Leu Ala Glu Cys Leu Leu Val Thr Thr
             195                 200                 205

Tyr Leu Leu Ile Ala Thr Ala Ala Leu Ala Val Pro Leu Pro Arg
         210                 215                 220

Gly Val Asn Ser Leu Gly Ala Pro Gln Val Ala Gly Ala Ala Thr Ala
225                 230                 235                 240

Val Leu Phe Leu Thr Leu Met Thr Arg Gly Gly Pro Arg Lys Arg His
                 245                 250                 255

Glu Leu Ala Ser Phe Ala Val Ile Thr Ala Ile Ala Val Ile Ala Ala
             260                 265                 270

Ala Ala Ala Phe Gly Tyr Gly Tyr Gln Asp Trp Val Pro Ala Gly Gly
             275                 280                 285

Ile Ala Phe Gly Leu Phe Ile Val Thr Asn Ala Ala Lys Leu Thr Val
 290                 295                 300

Ala Val Ala Arg Ile Ala Leu Pro Pro Ile Pro Val Pro Gly Glu Thr
305                 310                 315                 320

Val Asp Asn Glu Glu Leu Leu Asp Pro Val Ala Thr Pro Glu Ala Thr
                 325                 330                 335

Ser Glu Glu Thr Pro Thr Trp Gln Ala Ile Ile Ala Ser Val Pro Ala
             340                 345                 350

Ser Ala Val Arg Leu Thr Glu Arg Ser Lys Leu Ala Lys Gln Leu Leu
             355                 360                 365

Ile Gly Tyr Val Thr Ser Gly Thr Leu Ile Leu Ala Ala Gly Ala Ile
         370                 375                 380

Ala Val Val Val Arg Gly His Phe Phe Val His Ser Leu Val Val Ala
385                 390                 395                 400

Gly Leu Ile Thr Thr Val Cys Gly Phe Arg Ser Arg Leu Tyr Ala Glu
                 405                 410                 415

Arg Trp Cys Ala Trp Ala Leu Leu Ala Ala Thr Val Ala Ile Pro Thr
             420                 425                 430

Gly Leu Thr Ala Lys Leu Ile Ile Trp Tyr Pro His Tyr Ala Trp Leu
             435                 440                 445

Leu Leu Ser Val Tyr Leu Thr Val Ala Leu Val Ala Leu Val Val Val
```

```
                450                 455                 460
Gly Ser Met Ala His Val Arg Arg Val Ser Pro Val Lys Arg Thr
465                 470                 475                 480

Leu Glu Leu Ile Asp Gly Ala Met Ile Ala Ile Ile Pro Met Leu
                485                 490                 495

Leu Trp Ile Thr Gly Val Tyr Asp Thr Val Arg Asn Ile Arg Phe
                500                 505                 510

<210> SEQ ID NO 7
<211> LENGTH: 280
<212> TYPE: PRT
<213> ORGANISM: Mycobacterium tuberculosis

<400> SEQUENCE: 7

Met Ala Glu Pro Leu Ala Val Asp Pro Thr Gly Leu Ser Ala Ala
  1               5                  10                  15

Ala Lys Leu Ala Gly Leu Val Phe Pro Gln Pro Ala Pro Ile Ala
                 20                  25                  30

Val Ser Gly Thr Asp Ser Val Ala Ala Ile Asn Glu Thr Met Pro
                 35                  40                  45

Ser Ile Glu Ser Leu Val Ser Asp Gly Leu Pro Gly Val Lys Ala Ala
 50                  55                  60

Leu Thr Arg Thr Ala Ser Asn Met Asn Ala Ala Asp Val Tyr Ala
 65                  70                  75                  80

Lys Thr Asp Gln Ser Leu Gly Thr Ser Leu Ser Gln Tyr Ala Phe Gly
                 85                  90                  95

Ser Ser Gly Glu Gly Leu Ala Gly Ala Ser Val Gly Gly Gln Pro
                100                 105                 110

Ser Gln Ala Thr Gln Leu Leu Ser Thr Pro Val Ser Gln Val Thr Thr
                115                 120                 125

Gln Leu Gly Glu Thr Ala Ala Glu Leu Ala Pro Arg Val Val Ala Thr
                130                 135                 140

Val Pro Gln Leu Val Gln Leu Ala Pro His Ala Val Gln Met Ser Gln
145                 150                 155                 160

Asn Ala Ser Pro Ile Ala Gln Thr Ile Ser Gln Thr Ala Gln Gln Ala
                165                 170                 175

Ala Gln Ser Ala Gln Gly Gly Ser Gly Pro Met Pro Ala Gln Leu Ala
                180                 185                 190

Ser Ala Glu Lys Pro Ala Thr Glu Gln Ala Glu Pro Val His Glu Val
                195                 200                 205

Thr Asn Asp Asp Gln Gly Asp Gln Gly Asp Val Gln Pro Ala Glu Val
                210                 215                 220

Val Ala Ala Arg Asp Glu Gly Ala Gly Ser Pro Gly Gln Gln
225                 230                 235                 240

Pro Gly Gly Gly Val Pro Ala Gln Ala Met Asp Thr Gly Ala Gly Ala
                245                 250                 255

Arg Pro Ala Ala Ser Pro Leu Ala Ala Pro Val Asp Pro Ser Thr Pro
                260                 265                 270

Ala Pro Ser Thr Thr Thr Thr Leu
                275                 280

<210> SEQ ID NO 8
<211> LENGTH: 729
<212> TYPE: PRT
<213> ORGANISM: Mycobacterium tuberculosis
```

<400> SEQUENCE: 8

```
Met Ser Ile Thr Arg Pro Thr Gly Ser Tyr Ala Arg Gln Met Leu Asp
 1               5                  10                  15

Pro Gly Gly Trp Val Glu Ala Asp Glu Asp Thr Phe Tyr Asp Arg Ala
             20                  25                  30

Gln Glu Tyr Ser Gln Val Leu Gln Arg Val Thr Asp Val Leu Asp Thr
         35                  40                  45

Cys Arg Gln Gln Lys Gly His Val Phe Glu Gly Gly Leu Trp Ser Gly
     50                  55                  60

Gly Ala Ala Asn Ala Ala Asn Gly Ala Leu Gly Ala Asn Ile Asn Gln
 65                  70                  75                  80

Leu Met Thr Leu Gln Asp Tyr Leu Ala Thr Val Ile Thr Trp His Arg
                 85                  90                  95

His Ile Ala Gly Leu Ile Glu Gln Ala Lys Ser Asp Ile Gly Asn Asn
            100                 105                 110

Val Asp Gly Ala Gln Arg Glu Ile Asp Ile Leu Glu Asn Asp Pro Ser
        115                 120                 125

Leu Asp Ala Asp Glu Arg His Thr Ala Ile Asn Ser Leu Val Thr Ala
130                 135                 140

Thr His Gly Ala Asn Val Ser Leu Val Ala Glu Thr Ala Glu Arg Val
145                 150                 155                 160

Leu Glu Ser Lys Asn Trp Lys Pro Pro Lys Asn Ala Leu Glu Asp Leu
                165                 170                 175

Leu Gln Gln Lys Ser Pro Pro Pro Asp Val Pro Thr Leu Val Val
            180                 185                 190

Pro Ser Pro Gly Thr Pro Gly Thr Pro Gly Thr Pro Ile Thr Pro Gly
        195                 200                 205

Thr Pro Ile Thr Pro Gly Thr Pro Ile Thr Pro Ile Pro Gly Ala Pro
210                 215                 220

Val Thr Pro Ile Thr Pro Thr Pro Gly Thr Pro Val Thr Pro Val Thr
225                 230                 235                 240

Pro Gly Lys Pro Val Thr Pro Val Thr Pro Val Lys Pro Gly Thr Pro
                245                 250                 255

Gly Glu Pro Thr Pro Ile Thr Pro Val Thr Pro Pro Val Ala Pro Ala
            260                 265                 270

Thr Pro Ala Thr Pro Ala Thr Pro Val Thr Pro Ala Pro Ala Pro His
        275                 280                 285

Pro Gln Pro Ala Pro Ala Pro Ala Pro Ser Pro Gly Pro Gln Pro Val
        290                 295                 300

Thr Pro Ala Thr Pro Gly Pro Ser Gly Pro Ala Thr Pro Gly Thr Pro
305                 310                 315                 320

Gly Gly Glu Pro Ala Pro His Val Lys Pro Ala Ala Leu Ala Glu Gln
                325                 330                 335

Pro Gly Val Pro Gly Gln His Ala Gly Gly Thr Gln Ser Gly Pro
            340                 345                 350

Ala His Ala Asp Glu Ser Ala Ala Ser Val Thr Pro Ala Ala Ala Ser
            355                 360                 365

Gly Val Pro Gly Ala Arg Ala Ala Ala Ala Pro Ser Gly Thr Ala
        370                 375                 380

Val Gly Ala Gly Ala Arg Ser Ser Val Gly Thr Ala Ala Ala Ser Gly
385                 390                 395                 400

Ala Gly Ser His Ala Ala Thr Gly Arg Ala Pro Val Ala Thr Ser Asp
            405                 410                 415
```

-continued

```
Lys Ala Ala Ala Pro Ser Thr Arg Ala Ser Ala Arg Thr Ala Pro
                420                 425                 430

Pro Ala Arg Pro Pro Ser Thr Asp His Ile Asp Lys Pro Asp Arg Ser
            435                 440                 445

Glu Ser Ala Asp Asp Gly Thr Pro Val Ser Met Ile Pro Val Ser Ala
450                 455                 460

Ala Arg Ala Ala Arg Asp Ala Thr Ala Ala Ser Ala Arg Gln
465                 470                 475                 480

Arg Gly Arg Gly Asp Ala Leu Arg Leu Ala Arg Ile Ala Ala Ala
                485                 490                 495

Leu Asn Ala Ser Asp Asn Asn Ala Gly Asp Tyr Gly Phe Phe Trp Ile
                500                 505                 510

Thr Ala Val Thr Thr Asp Gly Ser Ile Val Val Ala Asn Ser Tyr Gly
            515                 520                 525

Leu Ala Tyr Ile Pro Asp Gly Met Glu Leu Pro Asn Lys Val Tyr Leu
530                 535                 540

Ala Ser Ala Asp His Ala Ile Pro Val Asp Glu Ile Ala Arg Cys Ala
545                 550                 555                 560

Thr Tyr Pro Val Leu Ala Val Gln Ala Trp Ala Ala Phe His Asp Met
                565                 570                 575

Thr Leu Arg Ala Val Ile Gly Thr Ala Glu Gln Leu Ala Ser Ser Asp
            580                 585                 590

Pro Gly Val Ala Lys Ile Val Leu Glu Pro Asp Asp Ile Pro Glu Ser
        595                 600                 605

Gly Lys Met Thr Gly Arg Ser Arg Leu Glu Val Val Asp Pro Ser Ala
610                 615                 620

Ala Ala Gln Leu Ala Asp Thr Thr Asp Gln Arg Leu Leu Asp Leu Leu
625                 630                 635                 640

Pro Pro Ala Pro Val Asp Val Asn Pro Pro Gly Asp Glu Arg His Met
                645                 650                 655

Leu Trp Phe Glu Leu Met Lys Pro Met Thr Ser Thr Ala Thr Gly Arg
            660                 665                 670

Glu Ala Ala His Leu Arg Ala Phe Arg Ala Tyr Ala Ala His Ser Gln
        675                 680                 685

Glu Ile Ala Leu His Gln Ala His Thr Ala Thr Asp Ala Ala Val Gln
690                 695                 700

Arg Val Ala Val Ala Asp Trp Leu Tyr Trp Gln Tyr Val Thr Gly Leu
705                 710                 715                 720

Leu Asp Arg Ala Leu Ala Ala Ala Cys
                725
```

<210> SEQ ID NO 9
<211> LENGTH: 1776
<212> TYPE: DNA
<213> ORGANISM: Mycobacterium tuberculosis
<220> FEATURE:
<221> NAME/KEY: CDS
<222> LOCATION: (1)...(1773)

<400> SEQUENCE: 9

```
atg act gct gaa ccg gaa gta cgg acg ctg cgc gag gtt gtg ctg gac      48
Met Thr Ala Glu Pro Glu Val Arg Thr Leu Arg Glu Val Val Leu Asp
 1               5                  10                  15 cag ctc ggc act gct gaa tcg cgt gcg tac aag atg tgg ctg ccg ccg      96
Gln Leu Gly Thr Ala Glu Ser Arg Ala Tyr Lys Met Trp Leu Pro Pro
             20                  25                  30
```

-continued

| | |
|---|---|
| ttg acc aat ccg gtc ccg ctc aac gag ctc atc gcc cgt gat cgg cga<br>Leu Thr Asn Pro Val Pro Leu Asn Glu Leu Ile Ala Arg Asp Arg Arg<br>        35                        40                        45 | 144 |
| caa ccc ctg cga ttt gcc ctg ggg atc atg gat gaa ccg cgc cgc cat<br>Gln Pro Leu Arg Phe Ala Leu Gly Ile Met Asp Glu Pro Arg Arg His<br>    50                        55                        60 | 192 |
| cta cag gat gtg tgg ggc gta gac gtt tcc ggg gcc ggc ggc aac atc<br>Leu Gln Asp Val Trp Gly Val Asp Val Ser Gly Ala Gly Gly Asn Ile<br>65                       70                        75                        80 | 240 |
| ggt att ggg ggc gca cct caa acc ggg aag tcg acg cta ctg cag acg<br>Gly Ile Gly Gly Ala Pro Gln Thr Gly Lys Ser Thr Leu Leu Gln Thr<br>                        85                        90                        95 | 288 |
| atg gtg atg tcg gcc gcc gcc aca cac tca ccg cgc aac gtt cag ttc<br>Met Val Met Ser Ala Ala Ala Thr His Ser Pro Arg Asn Val Gln Phe<br>100                                105                        110 | 336 |
| tat tgc atc gac cta ggt ggc ggc ggg ctg atc tat ctc gaa aac ctt<br>Tyr Cys Ile Asp Leu Gly Gly Gly Gly Leu Ile Tyr Leu Glu Asn Leu<br>            115                        120                        125 | 384 |
| cca cac gtc ggt ggg gta gcc aat cgg tcc gag ccc gac aag gtc aac<br>Pro His Val Gly Gly Val Ala Asn Arg Ser Glu Pro Asp Lys Val Asn<br>130                                135                        140 | 432 |
| cgg gtg gtc gca gag atg caa gcc gtc atg cgg caa cgg gaa acc acc<br>Arg Val Val Ala Glu Met Gln Ala Val Met Arg Gln Arg Glu Thr Thr<br>145                              150                        155                        160 | 480 |
| ttc aag gaa cac cga gtg ggc tcg atc ggg atg tac cgg cag ctg cgt<br>Phe Lys Glu His Arg Val Gly Ser Ile Gly Met Tyr Arg Gln Leu Arg<br>                       165                        170                        175 | 528 |
| gac gat cca agt caa ccc gtt gcg tcc gat cca tac ggc gac gtc ttt<br>Asp Asp Pro Ser Gln Pro Val Ala Ser Asp Pro Tyr Gly Asp Val Phe<br>            180                        185                        190 | 576 |
| ctg atc atc gac gga tgg ccc ggt ttt gtc ggc gag ttc ccc gac ctt<br>Leu Ile Ile Asp Gly Trp Pro Gly Phe Val Gly Glu Phe Pro Asp Leu<br>                    195                        200                        205 | 624 |
| gag ggg cag gtt caa gat ctg gcc gcc cag ggg ctg gcg ttc ggc gtc<br>Glu Gly Gln Val Gln Asp Leu Ala Ala Gln Gly Leu Ala Phe Gly Val<br>        210                        215                        220 | 672 |
| cac gtc atc atc tcc acg cca cgc tgg aca gag ctg aag tcg cgt gtt<br>His Val Ile Ile Ser Thr Pro Arg Trp Thr Glu Leu Lys Ser Arg Val<br>225                              230                        235                        240 | 720 |
| cgc gac tac ctc ggc acc aag atc gag ttc cgg ctt ggt gac gtc aat<br>Arg Asp Tyr Leu Gly Thr Lys Ile Glu Phe Arg Leu Gly Asp Val Asn<br>                       245                        250                        255 | 768 |
| gaa acc cag atc gac cgg att acc cgc gag atc ccg gcg aat cgt ccg<br>Glu Thr Gln Ile Asp Arg Ile Thr Arg Glu Ile Pro Ala Asn Arg Pro<br>            260                        265                        270 | 816 |
| ggt cgg gca gtg tcg atg gaa aag cac cat ctg atg atc ggc gtg ccc<br>Gly Arg Ala Val Ser Met Glu Lys His His Leu Met Ile Gly Val Pro<br>        275                        280                        285 | 864 |
| agg ttc gac ggc gtg cac agc gcc gat aac ctg gtg gag gcg atc acc<br>Arg Phe Asp Gly Val His Ser Ala Asp Asn Leu Val Glu Ala Ile Thr<br>            290                        295                        300 | 912 |
| gcg ggg gtg acg cag atc gct tcc cag cac acc gaa cag gca cct ccg<br>Ala Gly Val Thr Gln Ile Ala Ser Gln His Thr Glu Gln Ala Pro Pro<br>305                              310                        315                        320 | 960 |
| gtg cgg gtc ctg ccg gag cgt atc cac ctg cac gaa ctc gac ccg aac<br>Val Arg Val Leu Pro Glu Arg Ile His Leu His Glu Leu Asp Pro Asn<br>                       325                        330                        335 | 1008 |
| ccg ccg gga cca gag tcc gac tac cgc act cgc tgg gag att ccg atc<br>Pro Pro Gly Pro Glu Ser Asp Tyr Arg Thr Arg Trp Glu Ile Pro Ile | 1056 |

| | | | | | | | | | | | | | | | | |
|---|---|---|---|---|---|---|---|---|---|---|---|---|---|---|---|---|
| | | 340 | | | | 345 | | | | | 350 | | | | | |
| ggc | ttg | cgc | gag | acg | gac | ctg | acg | ccg | gct | cac | tgc | cac | atg | cac | acg | 1104 |
| Gly | Leu | Arg | Glu | Thr | Asp | Leu | Thr | Pro | Ala | His | Cys | His | Met | His | Thr | |
| | | 355 | | | | | 360 | | | | | 365 | | | | |
| aac | ccg | cac | cta | ctg | atc | ttc | ggt | gcg | gcc | aaa | tcg | ggc | aag | acg | acc | 1152 |
| Asn | Pro | His | Leu | Leu | Ile | Phe | Gly | Ala | Ala | Lys | Ser | Gly | Lys | Thr | Thr | |
| 370 | | | | | 375 | | | | | 380 | | | | | | |
| att | gcc | cac | gcg | atc | gcg | cgc | gcc | att | tgt | gcc | cga | aac | agt | ccc | cag | 1200 |
| Ile | Ala | His | Ala | Ile | Ala | Arg | Ala | Ile | Cys | Ala | Arg | Asn | Ser | Pro | Gln | |
| 385 | | | | 390 | | | | | 395 | | | | | 400 | | |
| cag | gtg | cgg | ttc | atg | ctc | gcg | gac | tac | cgc | tcg | ggc | ctg | ctg | gac | gcg | 1248 |
| Gln | Val | Arg | Phe | Met | Leu | Ala | Asp | Tyr | Arg | Ser | Gly | Leu | Leu | Asp | Ala | |
| | | | | 405 | | | | | 410 | | | | | 415 | | |
| gtg | ccg | gac | acc | cat | ctg | ctg | ggc | gcc | ggc | gcg | atc | aac | cgc | aac | agc | 1296 |
| Val | Pro | Asp | Thr | His | Leu | Leu | Gly | Ala | Gly | Ala | Ile | Asn | Arg | Asn | Ser | |
| | | 420 | | | | | 425 | | | | | 430 | | | | |
| gcg | tcg | cta | gac | gag | gcc | gtt | caa | gca | ctg | gcg | gtc | aac | ctg | aag | aag | 1344 |
| Ala | Ser | Leu | Asp | Glu | Ala | Val | Gln | Ala | Leu | Ala | Val | Asn | Leu | Lys | Lys | |
| | 435 | | | | | 440 | | | | | 445 | | | | | |
| cgg | ttg | ccg | ccg | acc | gac | ctg | acg | acg | gcg | cag | cta | cgc | tcg | cgt | tcg | 1392 |
| Arg | Leu | Pro | Pro | Thr | Asp | Leu | Thr | Thr | Ala | Gln | Leu | Arg | Ser | Arg | Ser | |
| 450 | | | | | 455 | | | | | 460 | | | | | | |
| tgg | tgg | agc | gga | ttt | gac | gtc | gtg | ctt | ctg | gtc | gac | gat | tgg | cac | atg | 1440 |
| Trp | Trp | Ser | Gly | Phe | Asp | Val | Val | Leu | Leu | Val | Asp | Asp | Trp | His | Met | |
| 465 | | | | 470 | | | | | 475 | | | | | 480 | | |
| atc | gtg | ggt | gcc | gcc | ggg | ggg | atg | ccg | ccg | atg | gca | ccg | ctg | gcc | ccg | 1488 |
| Ile | Val | Gly | Ala | Ala | Gly | Gly | Met | Pro | Pro | Met | Ala | Pro | Leu | Ala | Pro | |
| | | | | 485 | | | | | 490 | | | | | 495 | | |
| tta | ttg | ccg | gcg | gcg | gca | gat | atc | ggg | ttg | cac | atc | att | gtc | acc | tgt | 1536 |
| Leu | Leu | Pro | Ala | Ala | Ala | Asp | Ile | Gly | Leu | His | Ile | Ile | Val | Thr | Cys | |
| | | 500 | | | | | 505 | | | | | 510 | | | | |
| cag | atg | agc | cag | gct | tac | aag | gca | acc | atg | gac | aag | ttc | gtc | ggc | gcc | 1584 |
| Gln | Met | Ser | Gln | Ala | Tyr | Lys | Ala | Thr | Met | Asp | Lys | Phe | Val | Gly | Ala | |
| | | | | 515 | | | | | 520 | | | | | 525 | | |
| gca | ttc | ggg | tcg | ggc | gct | ccg | aca | atg | ttc | ctt | tcg | ggc | gag | aag | cag | 1632 |
| Ala | Phe | Gly | Ser | Gly | Ala | Pro | Thr | Met | Phe | Leu | Ser | Gly | Glu | Lys | Gln | |
| | 530 | | | | | 535 | | | | | 540 | | | | | |
| gaa | ttc | cca | tcc | agt | gag | ttc | aag | gtc | aag | cgg | cgc | ccc | cct | ggc | cag | 1680 |
| Glu | Phe | Pro | Ser | Ser | Glu | Phe | Lys | Val | Lys | Arg | Arg | Pro | Pro | Gly | Gln | |
| 545 | | | | | 550 | | | | | 555 | | | | | 560 | |
| gca | ttt | ctc | gtc | tcg | cca | gac | ggc | aaa | gag | gtc | atc | cag | gcc | ccc | tac | 1728 |
| Ala | Phe | Leu | Val | Ser | Pro | Asp | Gly | Lys | Glu | Val | Ile | Gln | Ala | Pro | Tyr | |
| | | | | 565 | | | | | 570 | | | | | 575 | | |
| atc | gag | cct | cca | gaa | gaa | gtg | ttc | gca | gca | ccc | cca | agc | gcc | ggt | | 1773 |
| Ile | Glu | Pro | Pro | Glu | Glu | Val | Phe | Ala | Ala | Pro | Pro | Ser | Ala | Gly | | |
| | | | 580 | | | | | 585 | | | | | 590 | | | |
| taa | | | | | | | | | | | | | | | | 1776 |

<210> SEQ ID NO 10
<211> LENGTH: 300
<212> TYPE: DNA
<213> ORGANISM: Mycobacterium tuberculosis
<220> FEATURE:
<221> NAME/KEY: CDS
<222> LOCATION: (1)...(297)

<400> SEQUENCE: 10

| | | | | | | | | | | | | | | | | |
|---|---|---|---|---|---|---|---|---|---|---|---|---|---|---|---|---|
| atg | gaa | aaa | atg | tca | cat | gat | ccg | atc | gct | gcc | gac | att | ggc | acg | caa | 48 |
| Met | Glu | Lys | Met | Ser | His | Asp | Pro | Ile | Ala | Ala | Asp | Ile | Gly | Thr | Gln | |
| 1 | | | | 5 | | | | | 10 | | | | | 15 | | |

-continued

| | |
|---|---|
| gtg agc gac aac gct ctg cac ggc gtg acg gcc ggc tcg acg gcg ctg<br>Val Ser Asp Asn Ala Leu His Gly Val Thr Ala Gly Ser Thr Ala Leu<br>20                        25                     30 | 96 |
| acg tcg gtg acc ggg ctg gtt ccc gcg ggg gcc gat gag gtc tcc gcc<br>Thr Ser Val Thr Gly Leu Val Pro Ala Gly Ala Asp Glu Val Ser Ala<br>           35                     40                     45 | 144 |
| caa gcg gcg acg gcg ttc aca tcg gag ggc atc caa ttg ctg gct tcc<br>Gln Ala Ala Thr Ala Phe Thr Ser Glu Gly Ile Gln Leu Leu Ala Ser<br>50                        55                     60 | 192 |
| aat gca tcg gcc caa gac cag ctc cac cgt gcg ggc gaa gcg gtc cag<br>Asn Ala Ser Ala Gln Asp Gln Leu His Arg Ala Gly Glu Ala Val Gln<br>65                        70                     75                     80 | 240 |
| gac gtc gcc cgc acc tat tcg caa atc gac gac ggc gcc gcc ggc gtc<br>Asp Val Ala Arg Thr Tyr Ser Gln Ile Asp Asp Gly Ala Ala Gly Val<br>           85                     90                     95 | 288 |
| ttc gcc gaa tag<br>Phe Ala Glu | 300 |

```
<210> SEQ ID NO 11
<211> LENGTH: 1107
<212> TYPE: DNA
<213> ORGANISM: Mycobacterium tuberculosis
<220> FEATURE:
<221> NAME/KEY: CDS
<222> LOCATION: (1)...(1104)

<400> SEQUENCE: 11
```

| | |
|---|---|
| atg ctg tgg cac gca atg cca ccg gag cta aat acc gca cgg ctg atg<br>Met Leu Trp His Ala Met Pro Pro Glu Leu Asn Thr Ala Arg Leu Met<br>1                        5                     10                     15 | 48 |
| gcc ggc gcg ggt ccg gct cca atg ctt gcg gcg gcc gcg gga tgg cag<br>Ala Gly Ala Gly Pro Ala Pro Met Leu Ala Ala Ala Ala Gly Trp Gln<br>                   20                     25                     30 | 96 |
| acg ctt tcg gcg gct ctg gac gct cag gcc gtc gag ttg acc gcg cgc<br>Thr Leu Ser Ala Ala Leu Asp Ala Gln Ala Val Glu Leu Thr Ala Arg<br>           35                     40                     45 | 144 |
| ctg aac tct ctg gga gaa gcc tgg act gga ggt ggc agc gac aag gcg<br>Leu Asn Ser Leu Gly Glu Ala Trp Thr Gly Gly Gly Ser Asp Lys Ala<br>50                        55                     60 | 192 |
| ctt gcg gct gca acg ccg atg gtg gtc tgg cta caa acc gcg tca aca<br>Leu Ala Ala Ala Thr Pro Met Val Val Trp Leu Gln Thr Ala Ser Thr<br>65                        70                     75                     80 | 240 |
| cag gcc aag acc cgt gcg atg cag gcg acg gcg caa gcc gcg gca tac<br>Gln Ala Lys Thr Arg Ala Met Gln Ala Thr Ala Gln Ala Ala Ala Tyr<br>           85                     90                     95 | 288 |
| acc cag gcc atg gcc acg acg ccg tcg ctg ccg gag atc gcc gcc aac<br>Thr Gln Ala Met Ala Thr Thr Pro Ser Leu Pro Glu Ile Ala Ala Asn<br>                   100                   105                   110 | 336 |
| cac atc acc cag gcc gtc ctt acg gcc acc aac ttc ttc ggt atc aac<br>His Ile Thr Gln Ala Val Leu Thr Ala Thr Asn Phe Phe Gly Ile Asn<br>           115                     120                   125 | 384 |
| acg atc ccg atc gcg ttg acc gag atg gat tat ttc atc cgt atg tgg<br>Thr Ile Pro Ile Ala Leu Thr Glu Met Asp Tyr Phe Ile Arg Met Trp<br>130                       135                   140 | 432 |
| aac cag gca gcc ctg gca atg gag gtc tac cag gcc gag acc gcg gtt<br>Asn Gln Ala Ala Leu Ala Met Glu Val Tyr Gln Ala Glu Thr Ala Val<br>145                     150                     155                   160 | 480 |
| aac acg ctt ttc gag aag ctc gag ccg atg gcg tcg atc ctt gat ccc<br>Asn Thr Leu Phe Glu Lys Leu Glu Pro Met Ala Ser Ile Leu Asp Pro<br>           165                     170                   175 | 528 |
| ggc gcg agc cag agc acg acg aac ccg atc ttc gga atg ccc tcc cct | 576 |

-continued

```
                    Gly Ala Ser Gln Ser Thr Thr Asn Pro Ile Phe Gly Met Pro Ser Pro
                                    180                 185                 190 ggc agc tca aca ccg gtt ggc cag ttg ccg ccg gcg gct acc cag acc              624
Gly Ser Ser Thr Pro Val Gly Gln Leu Pro Pro Ala Ala Thr Gln Thr
            195                 200                 205 ctc ggc caa ctg ggt gag atg agc ggc ccg atg cag cag ctg acc cag              672
Leu Gly Gln Leu Gly Glu Met Ser Gly Pro Met Gln Gln Leu Thr Gln
210                 215                 220 ccg ctg cag cag gtg acg tcg ttg ttc agc cag gtg ggc ggc acc ggc              720
Pro Leu Gln Gln Val Thr Ser Leu Phe Ser Gln Val Gly Gly Thr Gly
225                 230                 235                 240 ggc ggc aac cca gcc gac gag gaa gcc gcg cag atg ggc ctg ctc ggc              768
Gly Gly Asn Pro Ala Asp Glu Glu Ala Ala Gln Met Gly Leu Leu Gly
                245                 250                 255 acc agt ccg ctg tcg aac cat ccg ctg gct ggt gga tca ggc ccc agc              816
Thr Ser Pro Leu Ser Asn His Pro Leu Ala Gly Gly Ser Gly Pro Ser
            260                 265                 270 gcg ggc gcg ggc ctg ctg cgc gcg gag tcg cta cct ggc gca ggt ggg              864
Ala Gly Ala Gly Leu Leu Arg Ala Glu Ser Leu Pro Gly Ala Gly Gly
        275                 280                 285 tcg ttg acc cgc acg ccg ctg atg tct cag ctg atc gaa aag ccg gtt              912
Ser Leu Thr Arg Thr Pro Leu Met Ser Gln Leu Ile Glu Lys Pro Val
290                 295                 300 gcc ccc tcg gtg atg ccg gcg gct gcc gga tcg tcg gcg acg ggt              960
Ala Pro Ser Val Met Pro Ala Ala Ala Gly Ser Ser Ala Thr Gly
305                 310                 315                 320 ggc gcc gct ccg gtg ggt gcg gga gcg atg ggc cag ggt gcg caa tcc             1008
Gly Ala Ala Pro Val Gly Ala Gly Ala Met Gly Gln Gly Ala Gln Ser
                325                 330                 335 ggc ggc tcc acc agg ccg ggt ctg gtc gcg ccg gca ccg ctc gcg cag             1056
Gly Gly Ser Thr Arg Pro Gly Leu Val Ala Pro Ala Pro Leu Ala Gln
            340                 345                 350 gag cgt gaa gaa gac gac gag gac gac tgg gac gaa gag gac gac tgg             1104
Glu Arg Glu Glu Asp Asp Glu Asp Asp Trp Asp Glu Glu Asp Asp Trp
        355                 360                 365 tga                                                                         1107

<210> SEQ ID NO 12
<211> LENGTH: 303
<212> TYPE: DNA
<213> ORGANISM: Mycobacterium tuberculosis
<220> FEATURE:
<221> NAME/KEY: CDS
<222> LOCATION: (1)...(300)

<400> SEQUENCE: 12 atg gca gag atg aag acc gat gcc gct acc ctc gcg cag gag gca ggt               48
Met Ala Glu Met Lys Thr Asp Ala Ala Thr Leu Ala Gln Glu Ala Gly
1               5                   10                  15 aat ttc gag cgg atc tcc ggc gac ctg aaa acc cag atc gac cag gtg               96
Asn Phe Glu Arg Ile Ser Gly Asp Leu Lys Thr Gln Ile Asp Gln Val
                20                  25                  30 gag tcg acg gca ggt tcg ttg cag ggc cag tgg cgc ggc gcg gcg ggg              144
Glu Ser Thr Ala Gly Ser Leu Gln Gly Gln Trp Arg Gly Ala Ala Gly
            35                  40                  45 acg gcc gcc cag gcc gcg gtg gtg cgc ttc caa gaa gca gcc aat aag              192
Thr Ala Ala Gln Ala Ala Val Val Arg Phe Gln Glu Ala Ala Asn Lys
        50                  55                  60 cag aag cag gaa ctc gac gag atc tcg acg aat att cgt cag gcc ggc              240
Gln Lys Gln Glu Leu Asp Glu Ile Ser Thr Asn Ile Arg Gln Ala Gly
65                  70                  75                  80
```

```
gtc caa tac tcg agg gcc gac gag gag cag cag cag gcg ctg tcc tcg      288
Val Gln Tyr Ser Arg Ala Asp Glu Glu Gln Gln Gln Ala Leu Ser Ser
             85                  90                  95 caa atg ggc ttc tga                                                   303
Gln Met Gly Phe
        100

<210> SEQ ID NO 13
<211> LENGTH: 2001
<212> TYPE: DNA
<213> ORGANISM: Mycobacterium tuberculosis
<220> FEATURE:
<221> NAME/KEY: CDS
<222> LOCATION: (1)...(1998)

<400> SEQUENCE: 13 atg gcg gcc gac tac gac aag ctc ttc cgg ccg cac gaa ggt atg gaa       48
Met Ala Ala Asp Tyr Asp Lys Leu Phe Arg Pro His Glu Gly Met Glu
 1               5                  10                  15 gct ccg gac gat atg gca gcg cag ccg ttc ttc gac ccc agt gct tcg       96
Ala Pro Asp Asp Met Ala Ala Gln Pro Phe Phe Asp Pro Ser Ala Ser
             20                  25                  30 ttt ccg ccg gcg ccc gca tcg gca aac cta ccg aag ccc aac ggc cag      144
Phe Pro Pro Ala Pro Ala Ser Ala Asn Leu Pro Lys Pro Asn Gly Gln
         35                  40                  45 act ccg ccc ccg acg tcc gac gac ctg tcg gag cgg ttc gtg tcg gcc      192
Thr Pro Pro Pro Thr Ser Asp Asp Leu Ser Glu Arg Phe Val Ser Ala
     50                  55                  60 ccg ccg ccg cca ccc cca ccc cca cct ccg cct ccg cca act ccg atg      240
Pro Pro Pro Pro Pro Pro Pro Pro Pro Pro Pro Pro Thr Pro Met
 65                  70                  75                  80 ccg atc gcc gca gga gag ccg ccc tcg ccg gaa ccg gcc gca tct aaa      288
Pro Ile Ala Ala Gly Glu Pro Pro Ser Pro Glu Pro Ala Ala Ser Lys
                 85                  90                  95 cca ccc aca ccc ccc atg ccc atc gcc gga ccc gaa ccg gcc cca ccc      336
Pro Pro Thr Pro Pro Met Pro Ile Ala Gly Pro Glu Pro Ala Pro Pro
            100                 105                 110 aaa cca ccc aca ccc ccc atg ccc atc gcc gga ccc gaa ccg gcc cca      384
Lys Pro Pro Thr Pro Pro Met Pro Ile Ala Gly Pro Glu Pro Ala Pro
        115                 120                 125 ccc aaa cca ccc aca cct ccg atg ccc atc gcc gga cct gca ccc acc      432
Pro Lys Pro Pro Thr Pro Pro Met Pro Ile Ala Gly Pro Ala Pro Thr
    130                 135                 140 cca acc gaa tcc cag ttg gcg ccc ccc aga cca ccg aca cca caa acg      480
Pro Thr Glu Ser Gln Leu Ala Pro Pro Arg Pro Pro Thr Pro Gln Thr
145                 150                 155                 160 cca acc gga gcg ccg cag caa ccg gaa tca ccg gcg ccc cac gta ccc      528
Pro Thr Gly Ala Pro Gln Gln Pro Glu Ser Pro Ala Pro His Val Pro
                165                 170                 175 tcg cac ggg cca cat caa ccc cgg cgc acc gca cca gca ccg ccc tgg      576
Ser His Gly Pro His Gln Pro Arg Arg Thr Ala Pro Ala Pro Pro Trp
            180                 185                 190 gca aag atg cca atc ggc gaa ccc ccg ccc gct ccg tcc aga ccg tct      624
Ala Lys Met Pro Ile Gly Glu Pro Pro Pro Ala Pro Ser Arg Pro Ser
        195                 200                 205 gcg tcc ccg gcc gaa cca ccg acc cgg cct gcc ccc caa cac tcc cga      672
Ala Ser Pro Ala Glu Pro Pro Thr Arg Pro Ala Pro Gln His Ser Arg
    210                 215                 220 cgt gcg cgc cgg ggt cac cgc tat cgc aca gac acc gaa cga aac gtc      720
Arg Ala Arg Arg Gly His Arg Tyr Arg Thr Asp Thr Glu Arg Asn Val
225                 230                 235                 240
```

```
ggg aag gta gca act ggt cca tcc atc cag gcg cgg ctg cgg gca gag       768
Gly Lys Val Ala Thr Gly Pro Ser Ile Gln Ala Arg Leu Arg Ala Glu
            245                 250                 255 gaa gca tcc ggc gcg cag ctc gcc ccc gga acg gag ccc tcg cca gcg       816
Glu Ala Ser Gly Ala Gln Leu Ala Pro Gly Thr Glu Pro Ser Pro Ala
            260                 265                 270 ccg ttg ggc caa ccg aga tcg tat ctg gct ccg ccc acc cgc ccc gcg       864
Pro Leu Gly Gln Pro Arg Ser Tyr Leu Ala Pro Pro Thr Arg Pro Ala
        275                 280                 285 ccg aca gaa cct ccc ccc agc ccc tcg ccg cag cgc aac tcc ggt cgg       912
Pro Thr Glu Pro Pro Pro Ser Pro Ser Pro Gln Arg Asn Ser Gly Arg
        290                 295                 300 cgt gcc gag cga cgc gtc cac ccc gat tta gcc gcc caa cat gcc gcg       960
Arg Ala Glu Arg Arg Val His Pro Asp Leu Ala Ala Gln His Ala Ala
305                 310                 315                 320 gcg caa cct gat tca att acg gcc gca acc act ggc ggt cgt cgc cgc      1008
Ala Gln Pro Asp Ser Ile Thr Ala Ala Thr Thr Gly Gly Arg Arg Arg
                325                 330                 335 aag cgt gca gcg ccg gat ctc gac gcg aca cag aaa tcc tta agg ccg      1056
Lys Arg Ala Ala Pro Asp Leu Asp Ala Thr Gln Lys Ser Leu Arg Pro
            340                 345                 350 gcg gcc aag ggg ccg aag gtg aag aag gtg aag ccc cag aaa ccg aag      1104
Ala Ala Lys Gly Pro Lys Val Lys Lys Val Lys Pro Gln Lys Pro Lys
        355                 360                 365 gcc acg aag ccg ccc aaa gtg gtg tcg cag cgc ggc tgg cga cat tgg      1152
Ala Thr Lys Pro Pro Lys Val Val Ser Gln Arg Gly Trp Arg His Trp
        370                 375                 380 gtg cat gcg ttg acg cga atc aac ctg ggc ctg tca ccc gac gag aag      1200
Val His Ala Leu Thr Arg Ile Asn Leu Gly Leu Ser Pro Asp Glu Lys
385                 390                 395                 400 tac gag ctg gac ctg cac gct cga gtc cgc cgc aat ccc cgc ggg tcg      1248
Tyr Glu Leu Asp Leu His Ala Arg Val Arg Arg Asn Pro Arg Gly Ser
                405                 410                 415 tat cag atc gcc gtc gtc ggt ctc aaa ggt ggg gct ggc aaa acc acg      1296
Tyr Gln Ile Ala Val Val Gly Leu Lys Gly Gly Ala Gly Lys Thr Thr
            420                 425                 430 ctg aca gca gcg ttg ggg tcg acg ttg gct cag gtg cgg gcc gac cgg      1344
Leu Thr Ala Ala Leu Gly Ser Thr Leu Ala Gln Val Arg Ala Asp Arg
        435                 440                 445 atc ctg gct cta gac gcg gat cca ggc gcc gga aac ctc gcc gat cgg      1392
Ile Leu Ala Leu Asp Ala Asp Pro Gly Ala Gly Asn Leu Ala Asp Arg
        450                 455                 460 gta ggg cga caa tcg ggc gcg acc atc gct gat gtg ctt gca gaa aaa      1440
Val Gly Arg Gln Ser Gly Ala Thr Ile Ala Asp Val Leu Ala Glu Lys
465                 470                 475                 480 gag ctg tcg cac tac aac gac atc cgc gca cac act agc gtc aat gcg      1488
Glu Leu Ser His Tyr Asn Asp Ile Arg Ala His Thr Ser Val Asn Ala
                485                 490                 495 gtc aat ctg gaa gtg ctg ccg gca ccg gaa tac agc tcg gcg cag cgc      1536
Val Asn Leu Glu Val Leu Pro Ala Pro Glu Tyr Ser Ser Ala Gln Arg
            500                 505                 510 gcg ctc agc gac gcc gac tgg cat ttc atc gcc gat cct gcg tcg agg      1584
Ala Leu Ser Asp Ala Asp Trp His Phe Ile Ala Asp Pro Ala Ser Arg
        515                 520                 525 ttt tac aac ctc gtc ttg gct gat tgt ggg gcc ggc ttc ttc gac ccg      1632
Phe Tyr Asn Leu Val Leu Ala Asp Cys Gly Ala Gly Phe Phe Asp Pro
        530                 535                 540 ctg acc cgc ggc gtg ctg tcc acg gtg tcc ggt gtc gtg gtc gtg gca      1680
Leu Thr Arg Gly Val Leu Ser Thr Val Ser Gly Val Val Val Val Ala
```

-continued

```
            545                 550                 555                 560
agt gtc tca atc gac ggc gca caa cag gcg tcg gtc gcg ttg gac tgg          1728
Ser Val Ser Ile Asp Gly Ala Gln Gln Ala Ser Val Ala Leu Asp Trp
                565                 570                 575 ttg cgc aac aac ggt tac caa gat ttg gcg agc cgc gca tgc gtg gtc          1776
Leu Arg Asn Asn Gly Tyr Gln Asp Leu Ala Ser Arg Ala Cys Val Val
            580                 585                 590 atc aat cac atc atg ccg gga gaa ccc aat gtc gca gtt aaa gac ctg          1824
Ile Asn His Ile Met Pro Gly Glu Pro Asn Val Ala Val Lys Asp Leu
        595                 600                 605 gtg cgg cat ttc gaa cag caa gtt caa ccc ggc cgg gtc gtg gtc atg          1872
Val Arg His Phe Glu Gln Gln Val Gln Pro Gly Arg Val Val Val Met
    610                 615                 620 ccg tgg gac agg cac att gcg gcc gga acc gag att tca ctc gac ttg          1920
Pro Trp Asp Arg His Ile Ala Ala Gly Thr Glu Ile Ser Leu Asp Leu
625                 630                 635                 640 ctc gac cct atc tac aag cgc aag gtc ctc gaa ttg gcc gca gcg cta          1968
Leu Asp Pro Ile Tyr Lys Arg Lys Val Leu Glu Leu Ala Ala Ala Leu
                645                 650                 655 tcc gac gat ttc gag agg gct gga cgt cgt tga                              2001
Ser Asp Asp Phe Glu Arg Ala Gly Arg Arg
                660                 665

<210> SEQ ID NO 14
<211> LENGTH: 1536
<212> TYPE: DNA
<213> ORGANISM: Mycobacterium tuberculosis
<220> FEATURE:
<221> NAME/KEY: CDS
<222> LOCATION: (1)...(1533)

<400> SEQUENCE: 14 ttg agc gca cct gct gtt gct gct ggt cct acc gcc gcg ggg gca acc          48
Leu Ser Ala Pro Ala Val Ala Ala Gly Pro Thr Ala Ala Gly Ala Thr
 1               5                  10                  15 gct gcg cgg cct gcc acc acc cgg gtg acg atc ctg acc ggc aga cgg          96
Ala Ala Arg Pro Ala Thr Thr Arg Val Thr Ile Leu Thr Gly Arg Arg
            20                  25                  30 atg acc gat ttg gta ctg cca gcg gcg gtg ccg atg gaa act tat att          144
Met Thr Asp Leu Val Leu Pro Ala Ala Val Pro Met Glu Thr Tyr Ile
        35                  40                  45 gac gac acc gtc gcg gtg ctt tcc gag gtg ttg gaa gac acg ccg gct          192
Asp Asp Thr Val Ala Val Leu Ser Glu Val Leu Glu Asp Thr Pro Ala
    50                  55                  60 gat gta ctc ggc ggc ttc gac ttt acc gcg caa ggc gtg tgg gcg ttc          240
Asp Val Leu Gly Gly Phe Asp Phe Thr Ala Gln Gly Val Trp Ala Phe
65                  70                  75                  80 gct cgt ccc gga tcg ccg ccg ctg aag ctc gac cag tca ctc gat gac          288
Ala Arg Pro Gly Ser Pro Pro Leu Lys Leu Asp Gln Ser Leu Asp Asp
                85                  90                  95 gcc ggg gtg gtc gac ggg tca ctg ctg act ctg gtg tca gtc agt cgc          336
Ala Gly Val Val Asp Gly Ser Leu Leu Thr Leu Val Ser Val Ser Arg
            100                 105                 110 acc gag cgc tac cga ccg ttg gtc gag gat gtc atc gac gcg atc gcc          384
Thr Glu Arg Tyr Arg Pro Leu Val Glu Asp Val Ile Asp Ala Ile Ala
        115                 120                 125 gtg ctt gac gag tca cct gag ttc gac cgc acg gca ttg aat cgc ttt          432
Val Leu Asp Glu Ser Pro Glu Phe Asp Arg Thr Ala Leu Asn Arg Phe
    130                 135                 140 gtg ggg gcg gcg atc ccg ctt ttg acc gcg ccc gtc atc ggg atg gcg          480
Val Gly Ala Ala Ile Pro Leu Leu Thr Ala Pro Val Ile Gly Met Ala
```

```
                                      -continued 145                150                155                160 atg cgg gcg tgg tgg gaa act ggg cgt agc ttg tgg tgg ccg ttg gcg    528
Met Arg Ala Trp Trp Glu Thr Gly Arg Ser Leu Trp Trp Pro Leu Ala
                165                170                175 att ggc atc ctg ggg atc gct gtg ctg gta ggc agc ttc gtc gcg aac    576
Ile Gly Ile Leu Gly Ile Ala Val Leu Val Gly Ser Phe Val Ala Asn
                180                185                190 agg ttc tac cag agc ggc cac ctg gcc gag tgc cta ctg gtc acg acg    624
Arg Phe Tyr Gln Ser Gly His Leu Ala Glu Cys Leu Leu Val Thr Thr
                195                200                205 tat ctg ctg atc gca acc gcc gca gcg ctg gcc gtg ccg ttg ccg cgc    672
Tyr Leu Leu Ile Ala Thr Ala Ala Ala Leu Ala Val Pro Leu Pro Arg
        210                215                220 ggg gtc aac tcg ttg ggg gcg cca caa gtt gcc ggc gcc gct acg gcc    720
Gly Val Asn Ser Leu Gly Ala Pro Gln Val Ala Gly Ala Ala Thr Ala
225                230                235                240 gtg ctg ttt ttg acc ttg atg acg cgg ggc ggc cct cgg aag cgt cat    768
Val Leu Phe Leu Thr Leu Met Thr Arg Gly Gly Pro Arg Lys Arg His
                245                250                255 gag ttg gcg tcg ttt gcc gtg atc acc gct atc gcg gtc atc gcg gcc    816
Glu Leu Ala Ser Phe Ala Val Ile Thr Ala Ile Ala Val Ile Ala Ala
                260                265                270 gcc gct gcc ttc ggc tat gga tac cag gac tgg gtc ccc gcg ggg ggg    864
Ala Ala Ala Phe Gly Tyr Gly Tyr Gln Asp Trp Val Pro Ala Gly Gly
                275                280                285 atc gca ttc ggg ctg ttc att gtg acg aat gcg gcc aag ctg acc gtc    912
Ile Ala Phe Gly Leu Phe Ile Val Thr Asn Ala Ala Lys Leu Thr Val
                290                295                300 gcg gtc gcg cgg atc gcg ctg ccg ccg att ccg gta ccc ggc gaa acc    960
Ala Val Ala Arg Ile Ala Leu Pro Pro Ile Pro Val Pro Gly Glu Thr
305                310                315                320 gtg gac aac gag gag ttg ctc gat ccc gtc gcg acc ccg gag gct acc   1008
Val Asp Asn Glu Glu Leu Leu Asp Pro Val Ala Thr Pro Glu Ala Thr
                325                330                335 agc gaa gaa acc ccg acc tgg cag gcc atc atc gcg tcg gtg ccc gcg   1056
Ser Glu Glu Thr Pro Thr Trp Gln Ala Ile Ile Ala Ser Val Pro Ala
                340                345                350 tcc gcg gtc cgg ctc acc gag cgc agc aaa ctg gcc aag caa ctt ctg   1104
Ser Ala Val Arg Leu Thr Glu Arg Ser Lys Leu Ala Lys Gln Leu Leu
                355                360                365 atc gga tac gtc acg tcg ggc acc ctg att ctg gct gcc ggt gcc atc   1152
Ile Gly Tyr Val Thr Ser Gly Thr Leu Ile Leu Ala Ala Gly Ala Ile
                370                375                380 gcg gtc gtg gtg cgc ggg cac ttc ttt gta cac agc ctg gtg gtc gcg   1200
Ala Val Val Val Arg Gly His Phe Phe Val His Ser Leu Val Val Ala
385                390                395                400 ggt ttg atc acg acc gtc tgc gga ttt cgc tcg cgg ctt tac gcc gag   1248
Gly Leu Ile Thr Thr Val Cys Gly Phe Arg Ser Arg Leu Tyr Ala Glu
                405                410                415 cgc tgg tgt gcg tgg gcg ttg ctg gcg gcg acg gtc gcg att ccg acg   1296
Arg Trp Cys Ala Trp Ala Leu Leu Ala Ala Thr Val Ala Ile Pro Thr
                420                425                430 ggt ctg acg gcc aaa ctc atc atc tgg tac ccg cac tat gcc tgg ctg   1344
Gly Leu Thr Ala Lys Leu Ile Ile Trp Tyr Pro His Tyr Ala Trp Leu
                435                440                445 ttg ttg agc gtc tac ctc acg gta gcc ctg gtt gcg ctc gtg gtg gtc   1392
Leu Leu Ser Val Tyr Leu Thr Val Ala Leu Val Ala Leu Val Val Val
                450                455                460 ggg tcg atg gct cac gtc cgg cgc gtt tca ccg gtc gta aaa cga act   1440
```

```
Gly Ser Met Ala His Val Arg Arg Val Ser Pro Val Val Lys Arg Thr
465                 470                 475                 480 ctg gaa ttg atc gac ggc gcc atg atc gct gcc atc att ccc atg ctg      1488
Leu Glu Leu Ile Asp Gly Ala Met Ile Ala Ala Ile Ile Pro Met Leu
                    485                 490                 495 ctg tgg atc acc ggg gtg tac gac acg gtc cgc aat atc cgg ttc          1533
Leu Trp Ile Thr Gly Val Tyr Asp Thr Val Arg Asn Ile Arg Phe
                500                 505                 510 tga                                                                   1536

<210> SEQ ID NO 15
<211> LENGTH: 843
<212> TYPE: DNA
<213> ORGANISM: Mycobacterium tuberculosis
<220> FEATURE:
<221> NAME/KEY: CDS
<222> LOCATION: (1)...(840)

<400> SEQUENCE: 15 atg gct gaa ccg ttg gcc gtc gat ccc acc ggc ttg agc gca gcg gcc      48
Met Ala Glu Pro Leu Ala Val Asp Pro Thr Gly Leu Ser Ala Ala Ala
1               5                   10                  15 gcg aaa ttg gcc ggc ctc gtt ttt ccg cag cct ccg gcg ccg atc gcg      96
Ala Lys Leu Ala Gly Leu Val Phe Pro Gln Pro Pro Ala Pro Ile Ala
                20                  25                  30 gtc agc gga acg gat tcg gtg gta gca gca atc aac gag acc atg cca      144
Val Ser Gly Thr Asp Ser Val Val Ala Ala Ile Asn Glu Thr Met Pro
            35                  40                  45 agc atc gaa tcg ctg gtc agt gac ggg ctg ccc ggc gtg aaa gcc gcc      192
Ser Ile Glu Ser Leu Val Ser Asp Gly Leu Pro Gly Val Lys Ala Ala
        50                  55                  60 ctg act cga aca gca tcc aac atg aac gcg gcg gcg gac gtc tat gcg      240
Leu Thr Arg Thr Ala Ser Asn Met Asn Ala Ala Ala Asp Val Tyr Ala
65                  70                  75                  80 aag acc gat cag tca ctg gga acc agt ttg agc cag tat gca ttc ggc      288
Lys Thr Asp Gln Ser Leu Gly Thr Ser Leu Ser Gln Tyr Ala Phe Gly
                85                  90                  95 tcg tcg ggc gaa ggc ctg gct ggc gtc gcc tcg gtc ggt ggt cag cca      336
Ser Ser Gly Glu Gly Leu Ala Gly Val Ala Ser Val Gly Gly Gln Pro
                100                 105                 110 agt cag gct acc cag ctg ctg agc aca ccc gtg tca cag gtc acg acc      384
Ser Gln Ala Thr Gln Leu Leu Ser Thr Pro Val Ser Gln Val Thr Thr
            115                 120                 125 cag ctc ggc gag acg gcc gct gag ctg gca ccc cgt gtt gtt gcg acg      432
Gln Leu Gly Glu Thr Ala Ala Glu Leu Ala Pro Arg Val Val Ala Thr
        130                 135                 140 gtg ccg caa ctc gtt cag ctg gct ccg cac gcc gtt cag atg tcg caa      480
Val Pro Gln Leu Val Gln Leu Ala Pro His Ala Val Gln Met Ser Gln
145                 150                 155                 160 aac gca tcc ccc atc gct cag acg atc agt caa acc gcc caa cag gcc      528
Asn Ala Ser Pro Ile Ala Gln Thr Ile Ser Gln Thr Ala Gln Gln Ala
                165                 170                 175 gcc cag agc gcg cag ggc ggc agc ggc cca atg ccc gca cag ctt gcc      576
Ala Gln Ser Ala Gln Gly Gly Ser Gly Pro Met Pro Ala Gln Leu Ala
            180                 185                 190 agc gct gaa aaa ccg gcc acc gag caa gcg gag ccg gtc cac gaa gtg      624
Ser Ala Glu Lys Pro Ala Thr Glu Gln Ala Glu Pro Val His Glu Val
        195                 200                 205 aca aac gac gat cag ggc gac cag ggc gac gtg cag ccg gcc gag gtc      672
Thr Asn Asp Asp Gln Gly Asp Gln Gly Asp Val Gln Pro Ala Glu Val
210                 215                 220
```

```
gtt gcc gcg gca cgt gac gaa ggc gcc ggc gca tca ccg ggc cag cag      720
Val Ala Ala Ala Arg Asp Glu Gly Ala Gly Ala Ser Pro Gly Gln Gln
225                 230                 235                 240 ccc ggc ggg ggc gtt ccc gcg caa gcc atg gat acc gga gcc ggt gcc      768
Pro Gly Gly Gly Val Pro Ala Gln Ala Met Asp Thr Gly Ala Gly Ala
                245                 250                 255 cgc cca gcg gcg agt ccg ctg gcg gcc ccc gtc gat ccg tcg act ccg      816
Arg Pro Ala Ala Ser Pro Leu Ala Ala Pro Val Asp Pro Ser Thr Pro
        260                 265                 270 gca ccc tca aca acc aca acg ttg tag                                  843
Ala Pro Ser Thr Thr Thr Thr Leu
            275                 280

<210> SEQ ID NO 16
<211> LENGTH: 2190
<212> TYPE: DNA
<213> ORGANISM: Mycobacterium tuberculosis
<220> FEATURE:
<221> NAME/KEY: CDS
<222> LOCATION: (1)...(2187)

<400> SEQUENCE: 16 atg agt att acc agg ccg acg ggc agc tat gcc aga cag atg ctg gat       48
Met Ser Ile Thr Arg Pro Thr Gly Ser Tyr Ala Arg Gln Met Leu Asp
1               5                   10                  15 ccg ggc ggc tgg gtg gaa gcc gat gaa gac act ttc tat gac cgg gcc       96
Pro Gly Gly Trp Val Glu Ala Asp Glu Asp Thr Phe Tyr Asp Arg Ala
                20                  25                  30 cag gaa tat agc cag gtt ttg caa agg gtc acc gat gta ttg gac acc      144
Gln Glu Tyr Ser Gln Val Leu Gln Arg Val Thr Asp Val Leu Asp Thr
            35                  40                  45 tgc cgc cag cag aaa ggc cac gtc ttc gaa ggc ggc cta tgg tcc ggc      192
Cys Arg Gln Gln Lys Gly His Val Phe Glu Gly Gly Leu Trp Ser Gly
        50                  55                  60 ggc gcc gcc aat gct gcc aac ggc gcc ctg ggt gca aac atc aat caa      240
Gly Ala Ala Asn Ala Ala Asn Gly Ala Leu Gly Ala Asn Ile Asn Gln
65                  70                  75                  80 ttg atg acg ctg cag gat tat ctc gcc acg gtg att acc tgg cac agg      288
Leu Met Thr Leu Gln Asp Tyr Leu Ala Thr Val Ile Thr Trp His Arg
                85                  90                  95 cat att gcc ggg ttg att gag caa gct aaa tcc gat atc ggc aat aat      336
His Ile Ala Gly Leu Ile Glu Gln Ala Lys Ser Asp Ile Gly Asn Asn
                100                 105                 110 gtg gat ggc gct caa cgg gag atc gat atc ctg gag aat gac cct agc      384
Val Asp Gly Ala Gln Arg Glu Ile Asp Ile Leu Glu Asn Asp Pro Ser
            115                 120                 125 ctg gat gct gat gag cgc cat acc gcc atc aat tca ttg gtc acg gcg      432
Leu Asp Ala Asp Glu Arg His Thr Ala Ile Asn Ser Leu Val Thr Ala
        130                 135                 140 acg cat ggg gcc aat gtc agt ctg gtc gcc gag acc gct gag cgg gtg      480
Thr His Gly Ala Asn Val Ser Leu Val Ala Glu Thr Ala Glu Arg Val
145                 150                 155                 160 ctg gaa tcc aag aat tgg aaa cct ccg aag aac gca ctc gag gat ttg      528
Leu Glu Ser Lys Asn Trp Lys Pro Pro Lys Asn Ala Leu Glu Asp Leu
                165                 170                 175 ctt cag cag aag tcg ccg cca ccc cca gac gtg cct acc ctg gtc gtg      576
Leu Gln Gln Lys Ser Pro Pro Pro Asp Val Pro Thr Leu Val Val
                180                 185                 190 cca tcc ccg ggc aca ccg ggc aca ccg gga acc ccg atc acc ccg gga      624
Pro Ser Pro Gly Thr Pro Gly Thr Pro Gly Thr Pro Ile Thr Pro Gly
            195                 200                 205
```

```
acc ccg atc acc ccg gga acc cca atc aca ccc atc ccg gga gcg ccg      672
Thr Pro Ile Thr Pro Gly Thr Pro Ile Thr Pro Ile Pro Gly Ala Pro
    210             215             220 gta act ccg atc aca cca acg ccc ggc act ccc gtc acg ccg gtg acc      720
Val Thr Pro Ile Thr Pro Thr Pro Gly Thr Pro Val Thr Pro Val Thr
225             230             235             240 ccg ggc aag ccg gtc acc ccg gtg acc ccg gtc aaa ccg ggc aca cca      768
Pro Gly Lys Pro Val Thr Pro Val Thr Pro Val Lys Pro Gly Thr Pro
                245             250             255 ggc gag cca acc ccg atc acg ccg gtc acc ccc gtc gcc ccg gcc          816
Gly Glu Pro Thr Pro Ile Thr Pro Val Thr Pro Pro Val Ala Pro Ala
            260             265             270 aca ccg gca acc ccg gcc acg ccc gtt acc cca gct ccc gct cca cac      864
Thr Pro Ala Thr Pro Ala Thr Pro Val Thr Pro Ala Pro Ala Pro His
        275             280             285 ccg cag ccg gct ccg gca ccg gcg cca tcg cct ggg ccc cag ccg gtt      912
Pro Gln Pro Ala Pro Ala Pro Ala Pro Ser Pro Gly Pro Gln Pro Val
    290             295             300 aca ccg gcc act ccc ggt ccg tct ggt cca gca aca ccg ggc acc cca      960
Thr Pro Ala Thr Pro Gly Pro Ser Gly Pro Ala Thr Pro Gly Thr Pro
305             310             315             320 ggg ggc gag ccg gcg ccg cac gtc aaa ccc gcg gcg ttg gcg gag caa     1008
Gly Gly Glu Pro Ala Pro His Val Lys Pro Ala Ala Leu Ala Glu Gln
                325             330             335 cct ggt gtg ccg ggc cag cat gcg ggc ggg ggg acg cag tcg ggg cct     1056
Pro Gly Val Pro Gly Gln His Ala Gly Gly Gly Thr Gln Ser Gly Pro
            340             345             350 gcc cat gcg gac gaa tcc gcc gcg tcg gtg acg ccg gct gcg gcg tcc     1104
Ala His Ala Asp Glu Ser Ala Ala Ser Val Thr Pro Ala Ala Ala Ser
        355             360             365 ggt gtc ccg ggc gca cgg gcg gcg gcc gcg ccg agc ggt acc gcc         1152
Gly Val Pro Gly Ala Arg Ala Ala Ala Ala Pro Ser Gly Thr Ala
    370             375             380 gtg gga gcg ggc gcg cgt tcg agc gtg ggt acg gcc gcg gcc tcg ggc     1200
Val Gly Ala Gly Ala Arg Ser Ser Val Gly Thr Ala Ala Ala Ser Gly
385             390             395             400 gcg ggg tcg cat gct gcc act ggg cgg gcg ccg gtg gct acc tcg gac     1248
Ala Gly Ser His Ala Ala Thr Gly Arg Ala Pro Val Ala Thr Ser Asp
                405             410             415 aag gcg gcg gca ccg agc acg cgg gcg gcc tcg gcg cgg acg gca cct     1296
Lys Ala Ala Ala Pro Ser Thr Arg Ala Ala Ser Ala Arg Thr Ala Pro
            420             425             430 cct gcc cgc ccg ccg tcg acc gat cac atc gac aaa ccc gat cgc agc     1344
Pro Ala Arg Pro Pro Ser Thr Asp His Ile Asp Lys Pro Asp Arg Ser
        435             440             445 gag tct gca gat gac ggt acg ccg gtg tcg atg atc ccg gtg tcg gcg     1392
Glu Ser Ala Asp Asp Gly Thr Pro Val Ser Met Ile Pro Val Ser Ala
    450             455             460 gct cgg gcg gca cgc gac gcc gcc act gca gct gcc agc gcc cgc cag     1440
Ala Arg Ala Ala Arg Asp Ala Ala Thr Ala Ala Ala Ser Ala Arg Gln
465             470             475             480 cgt ggc cgc ggt gat gcg ctg cgg ttg gcg cga cgc atc gcg gcg gcg     1488
Arg Gly Arg Gly Asp Ala Leu Arg Leu Ala Arg Arg Ile Ala Ala Ala
                485             490             495 ctc aac gcg tcc gac aac aac gcg ggc gac tac ggg ttc ttc tgg atc     1536
Leu Asn Ala Ser Asp Asn Asn Ala Gly Asp Tyr Gly Phe Phe Trp Ile
            500             505             510 acc gcg gtg acc acc gac ggt tcc atc gtc gtg gcc aac agc tat ggg     1584
Thr Ala Val Thr Thr Asp Gly Ser Ile Val Val Ala Asn Ser Tyr Gly
```

-continued

| | | | | | | | | | | | | | | | |
|---|---|---|---|---|---|---|---|---|---|---|---|---|---|---|---|
| | | 515 | | | | | 520 | | | | | 525 | | | |
| ctg | gcc | tac | ata | ccc | gac | ggg | atg | gaa | ttg | ccg | aat | aag | gtg | tac | ttg | 1632 |
| Leu | Ala | Tyr | Ile | Pro | Asp | Gly | Met | Glu | Leu | Pro | Asn | Lys | Val | Tyr | Leu |
| | | 530 | | | | | 535 | | | | | 540 | | | |
| gcc | agc | gcg | gat | cac | gca | atc | ccg | gtt | gac | gaa | att | gca | cgc | tgt | gcc | 1680 |
| Ala | Ser | Ala | Asp | His | Ala | Ile | Pro | Val | Asp | Glu | Ile | Ala | Arg | Cys | Ala |
| 545 | | | | 550 | | | | | 555 | | | | | 560 | |
| acc | tac | ccg | gtt | ttg | gcc | gtg | caa | gcc | tgg | gcg | gct | ttc | cac | gac | atg | 1728 |
| Thr | Tyr | Pro | Val | Leu | Ala | Val | Gln | Ala | Trp | Ala | Ala | Phe | His | Asp | Met |
| | | | | 565 | | | | | 570 | | | | | 575 | |
| acg | ctg | cgg | gcg | gtg | atc | ggt | acc | gcg | gag | cag | ttg | gcc | agt | tcg | gat | 1776 |
| Thr | Leu | Arg | Ala | Val | Ile | Gly | Thr | Ala | Glu | Gln | Leu | Ala | Ser | Ser | Asp |
| | | | 580 | | | | | 585 | | | | | 590 | | |
| ccc | ggt | gtg | gcc | aag | att | gtg | ctg | gag | cca | gat | gac | att | ccg | gag | agc | 1824 |
| Pro | Gly | Val | Ala | Lys | Ile | Val | Leu | Glu | Pro | Asp | Asp | Ile | Pro | Glu | Ser |
| | | 595 | | | | | 600 | | | | | 605 | | | |
| ggc | aaa | atg | acg | ggc | cgg | tcg | cgg | ctg | gag | gtc | gtc | gac | ccc | tcg | gcg | 1872 |
| Gly | Lys | Met | Thr | Gly | Arg | Ser | Arg | Leu | Glu | Val | Val | Asp | Pro | Ser | Ala |
| | 610 | | | | | 615 | | | | | 620 | | | | |
| gcg | gct | cag | ctg | gcc | gac | act | acc | gat | cag | cgt | ttg | ctc | gac | ttg | ttg | 1920 |
| Ala | Ala | Gln | Leu | Ala | Asp | Thr | Thr | Asp | Gln | Arg | Leu | Leu | Asp | Leu | Leu |
| 625 | | | | 630 | | | | | 635 | | | | | 640 | |
| ccg | ccg | gcg | ccg | gtg | gat | gtc | aat | cca | ccg | ggc | gat | gag | cgg | cac | atg | 1968 |
| Pro | Pro | Ala | Pro | Val | Asp | Val | Asn | Pro | Pro | Gly | Asp | Glu | Arg | His | Met |
| | | | | 645 | | | | | 650 | | | | | 655 | |
| ctg | tgg | ttc | gag | ctg | atg | aag | ccc | atg | acc | agc | acc | gct | acc | ggc | cgc | 2016 |
| Leu | Trp | Phe | Glu | Leu | Met | Lys | Pro | Met | Thr | Ser | Thr | Ala | Thr | Gly | Arg |
| | | | 660 | | | | | 665 | | | | | 670 | | |
| gag | gcc | gct | cat | ctg | cgg | gcg | ttc | cgg | gcc | tac | gct | gcc | cac | tca | cag | 2064 |
| Glu | Ala | Ala | His | Leu | Arg | Ala | Phe | Arg | Ala | Tyr | Ala | Ala | His | Ser | Gln |
| | | 675 | | | | | 680 | | | | | 685 | | | |
| gag | att | gcc | ctg | cac | caa | gcg | cac | act | gcg | act | gac | gcg | gcc | gtc | cag | 2112 |
| Glu | Ile | Ala | Leu | His | Gln | Ala | His | Thr | Ala | Thr | Asp | Ala | Ala | Val | Gln |
| | 690 | | | | | 695 | | | | | 700 | | | | |
| cgt | gtg | gcc | gtc | gcg | gac | tgg | ctg | tac | tgg | caa | tac | gtc | acc | ggg | ttg | 2160 |
| Arg | Val | Ala | Val | Ala | Asp | Trp | Leu | Tyr | Trp | Gln | Tyr | Val | Thr | Gly | Leu |
| 705 | | | | 710 | | | | | 715 | | | | | 720 | |
| ctc | gac | cgg | gcc | ctg | gcc | gcc | gca | tgc | tga | | | | | | | 2190 |
| Leu | Asp | Arg | Ala | Leu | Ala | Ala | Ala | Cys | | | | | | | |
| | | | | 725 | | | | | | | | | | | |